United States Patent [19]

Lüthy et al.

[11] Patent Number: 4,871,757
[45] Date of Patent: Oct. 3, 1989

[54] HETEROCYCLIC COMPOUNDS

[75] Inventors: Christoph Lüthy, Schwerzenbach; René Zurflüh, Bülach, both of Switzerland

[73] Assignee: Hoffmann-La Roche Inc., Nutley, N.J.

[21] Appl. No.: 882,102

[22] Filed: Jul. 3, 1986

[30] Foreign Application Priority Data

Jul. 12, 1985 [CH]  Switzerland .......................... 3042/85
Apr. 29, 1986 [CH]  Switzerland .......................... 1748/86

[51] Int. Cl.$^4$ ................. A01N 43/653; C07D 249/10
[52] U.S. Cl. ..................................... 514/383; 548/262
[58] Field of Search ................. 548/262; 514/383; 71/92

[56] References Cited

U.S. PATENT DOCUMENTS 4,097,599  6/1978  Evans et al. .......................... 424/263
4,338,119  7/1982  Stetter et al. ........................... 71/92
4,414,221  11/1983  Parsons et al. ....................... 424/269
4,717,734  6/1988  Rogers et al. ........................ 514/359

*Primary Examiner*—Glennon H. Hollrah
*Assistant Examiner*—Peter G. O'Sullivan
*Attorney, Agent, or Firm*—Jon S. Saxe; George M. Gould; Dennis P. Tramaloni

[57] ABSTRACT

The invention is concerned with novel triazole derivatives of the formula

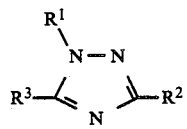

I wherein $R^1$ is optionally substituted phenyl and $R^2$ signifies substituted phenyl, as more precisely defined in the description, and $R^3$ is halogen, methyl or halomethyl, and their acid addition salts, processes for their preparation, pest control compositions which contain these compounds as the active substance, as well as methods of use of such compounds or compositions for the control of pests.

42 Claims, No Drawings

HETEROCYCLIC COMPOUNDS

DETAILED DESCRIPTION OF THE INVENTION

The present invention is concerned with heterocyclic compounds, namely 1,2,4-triazoles of the formula

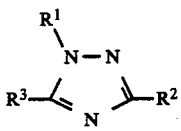

I wherein
$R^1$ is phenyl or phenyl substituted with 1 to 3 chlorine atoms, a bromine atom, an iodine atom, 1 to 3 fluorine atoms, 1 or 2 $C_{1-2}$-alkyl groups, 1 or 2 halomethyl groups, a $C_{1-2}$-alkoxy group, a $C_{1-2}$-haloalkoxy group, a nitro group and/or a cyano group.
$R^2$ is phenyl substituted with 1 or 2 chlorine atoms, a bromine atom, an iodine atom, 1 to 3 fluorine atoms, 1 or 2 $C_{1-2}$-alkyl groups, a halomethyl group and/or 1 or 2 methoxy groups, at least one of the substituents being situated in an o-position, and
$R^3$ is halogen, methyl or halomethyl,
as well as the acid addition salts of the compounds of formula I.

The compounds of formula I and their acid addition salts are pest control agents and are especially suitable for the control of insects and mites, e.g. spider mites. Accordingly, the invention also embraces pest control compositions which contain compounds of formula I or acid addition salts thereof as the active substance, processes for the manufacture of these compounds, and methods of use of these compounds or compositions for the control of pests.

The term "halogen" used in the above definition of the compounds of formula I embraces fluorine, chlorine, bromine and iodine. The "halomethyl" and "$C_{1-2}$-haloalkoxy" groups can in each case have one or more (the same or different) halogen substituents. The substituents in the substituted phenyl group $R^1$ or $R^2$ can also be the same or different.

Acid addition salts of the compounds of formula I include any of the physiologically compatible salts, such as salts of these compounds with inorganic or organic acids, preferably hydrohalic acids such as hydrochloric acid and hydrobromic acid; nitric acid; phosphoric acid; sulfuric acid; mono- and bifunctional carboxylic acids and hydroxycarboxylic acids such as trifluoroacetic acid and oxalic acid; and sulfonic acids such as fluorosulfonic acid.

A particular sub-group of the compounds of formula I are those in which $R^1$ is phenyl substituted as described above, and in which at least one of the substituents is situated in an o-position, and $R^2$ and $R^3$ have the significances given above. A further particular sub-group consists of those compounds of formula I in which $R^3$ signifies halogen, especially chlorine, and $R^1$ and $R^2$ have the significances given above.

$R^1$ is preferably unsubstituted phenyl or a mono- or disubstituted phenyl group in which the substituent(s) is/are one or two fluorine atoms, one or two chlorine atoms, a bromine atom, an iodine atom, one or two $C_{1-2}$-alkyl groups and/or a trifluoromethyl group, the substituent or one of the two substituents being preferably situated in the o-position. Especially preferred substituents in the o-position are fluorine, chlorine, bromine, methyl and trifluoromethyl.

Independently of the significance of $R^1$, $R^2$ is preferably a mono- or disubstituted phenyl group in which the substituents(s) is/are one or two fluorine atoms, one or two chlorine atoms, a bromine atom and/or an iodine atom. Especially preferably, $R^2$ signifies o-chlorophenyl, 2-chloro-4-fluorophenyl, 2-chloro-6-fluorophenyl or 2,6-difluorophenyl.

Independently of the significances of $R^1$ and $R^2$, $R^3$ is preferably fluorine, chlorine, bromine or methyl. Especially preferably, $R^3$ is chlorine.

Preferred individual compounds of formula I are:
1,3-Bis-(o-chlorophenyl)-5-chloro-1H-1,2,4-triazole,
5-chloro-3-(o-chlorophenyl)-1-($\alpha,\alpha,\alpha$-trifluoro-o-tolyl)-1H-1,2,4-triazole,
5-chloro-3-(2,6-difluorophenyl)-1-($\alpha,\alpha,\alpha$-trifluoro-o-tolyl)-1H-1,2,4-triazole,
5-chloro-1-(o-chlorophenyl)-3-(2-chloro-4-fluorophenyl)-1H-1,2,4-triazole,
5-chloro-1-(o-chlorophenyl)-3-(2,6-difluorophenyl)-1H-1,2,4-triazole,
5-chloro-3-(2-chloro-4-fluorophenyl)-1-($\alpha,\alpha,\alpha$-trifluoro-o-tolyl)-1H-1,2,4-triazole,
5-chloro-3-(2-chloro-6-fluorophenyl)-1-($\alpha,\alpha,\alpha$-trifluoro-o-tolyl)-1H-1,2,4-triazole,
5-chloro-1-(o-chlorophenyl)-3-(2-chloro-6-fluorophenyl)-1H-1,2,4-triazole,
5-bromo-3-(2,6-difluorophenyl)-1-($\alpha,\alpha,\alpha$-trifluoro-o-tolyl)-1H-1,2,4-triazole,
3-(o-chlorophenyl)-5-methyl-1-($\alpha,\alpha,\alpha$-trifluoro-o-tolyl)-1H-1,2,4-triazole,
3-(2-chloro-4-fluorophenyl)-5-methyl-1-($\alpha,\alpha,\alpha$-trifluoro-o-tolyl)-1H-1,2,4-triazole,
3-(2,6-difluorophenyl)-5-methyl-1-($\alpha,\alpha,\alpha$-trifluoro-o-tolyl)-1H-1,2,4-triazole,
3-(2-chloro-6-fluorophenyl)-5-methyl-1-($\alpha,\alpha,\alpha$-trifluoro-o-tolyl)-1H-1,2,4-triazole,
5-chloro-3-(o-chlorophenyl)-1-(o-tolyl)-1H-1,2,4-triazole,
5-chloro-3-(o-chlorophenyl)-1-(3-chloro-o-tolyl)-1H-1,2,4-triazole,
5-chloro-3-(o-chlorophenyl)-1-(5-chloro-o-tolyl)-1H-1,2,4-triazole,
5-chloro-3-(2,6-difluorophenyl)-1-(o-tolyl)-1H-1,2,4-triazole,
5-chloro-3-(2,6-difluorophenyl)-1-phenyl-1H-1,2,4-triazole,
5-chloro-3-(2,6-difluorophenyl)-1-(3-chloro-o-tolyl)-1H-1,2,4-triazole,
5-chloro-3-(2-chloro-6-fluorophenyl)-1-(3-chloro-o-tolyl)-1H-1,2,4-triazole,
1-(o-bromophenyl)-5-chloro-3-(2,6-difluorophenyl)-1H-1,2,4-triazole,
5-chloro-3-(o-chlorophenyl)-1-(o-fluorophenyl)-1H-1,2,4-triazole and
3-(2-chloro-6-fluorophenyl)-5-fluoro-1-($\alpha,\alpha,\alpha$-trifluoro-o-tolyl)-1H-1,2,4-triazole.

Further representatives of compounds of formula I are:
3-(2,6-Difluorophenyl)-5-fluoro-1-($\alpha,\alpha,\alpha$-trifluoro-o-tolyl)-1H-1,2,4-triazole,
3-(2,6-difluorophenyl)-1-(o-tolyl)-5-trifluoromethyl-1H-1,2,4-triazole,
1-(o-ethylphenyl)-5-chloro-3-(2,6-difluorophenyl)-1H-1,2,4-triazole,
5-chloro-1-(5-chloro-2-trifluoromethylphenyl)-3-(2,6-difluorophenyl)-1H-1,2,4-triazole, 5-chloro-1-(2-chloro-5-trifluoromethylphenyl)-3-(2,6-difluorophenyl)-1H-1,2,4-triazole,
5-chloro-1-(2-chloro-4-trifluoromethylphenyl)-3-(2,6-difluorophenyl)-1H-1,2,4-triazole,
1-(o-cyanophenyl)-3-(2,6-difluorophenyl)-5-methyl-1H-1,2,4-triazole,
5-chloro-1-(3,5dichloro-2,4-difluorophenyl)-3-(2,6-difluorophenyl)-1H-1,2,4-triazole,
5-chloro-3-(2,6-difluorophenyl)-1-(o-trifluoromethoxyphenyl)-1H-1,2,4-triazole,
5-chloro-3-(2,6-difluorophenyl)-1-(α,α-difluoro-o-tolyl)-1H-1,2,4-triazole,
3-(o-bromophenyl)-5-chloro-1-(o-chlorophenyl)-1H-1,2,4-triazole,
5-chloro-3-(2,3-dichlorophenyl)-1-(α,α,α-trifluoro-o-tolyl)-1H-1,2,4-triazole,
5-chloro-3-(2-chloro-4,6-difluorophenyl)-1-(α,α,α-trifluoro-o-tolyl)-1H-1,2,4-triazole,
5-chloro-1-(2-chloro-5-nitrophenyl)-3-(2-chlorophenyl)-1H-1,2,4-triazole,
5-chloro-3-(o-chlorophenyl)-1-(4-nitro-2-trifluoromethylphenyl)-1H-1,2,4-triazole,
1,3-bis-(o-chlorophenyl)-5-fluoro-1H-1,2,4-triazole,
5-chloro-3-(o-methoxyphenyl)-1-(α,α,α-trifluoro-o-tolyl)-1H-1,2,4-triazole,
3-(2-chloro-4-fluorophenyl)-5-fluoro-1-(α,α,α-trifluoro-o-tolyl)-1H-1,2,4-triazole,
1-(o-chlorophenyl)-3-(2-chloro-6-fluorophenyl)-5-fluoro-1H-1,2,4-triazole,
5-chloro-3-(2,6-difluorophenyl)-1-(o-fluorophenyl)-1H-1,2,4-triazole,
5-bromo-1-(o-chlorophenyl)-3-(2,6-difluorophenyl)-1H-1,2,4-triazole,
1-(o-chlorophenyl)-3-(2,6-difluorophenyl)-5-fluoro-1H-1,2,4-triazole,
5-chloro-1-(o-chlorophenyl)-3-(2,4,6-trifluorophenyl)-1H-,1,2,4-triazole,
5-chloro-3-(2,4,6-trifluorophenyl)-1-(α,α,α-trifluoro-o-tolyl)-1H-1,2,4-triazole,
5-chloro-1-(α,α,α-chlorodifluoro-o-tolyl)-3-(2,6-difluorophenyl)-1H-1,2,4-triazole,
3-(o-chlorophenyl)-5-trifluoromethyl-1-(α,α,α-trifluoro-o-tolyl)-1H-1,2,4-triazole,
5-chloro-1-(o-chlorophenyl)-3-(o-tolyl)-1H-1,2,4-triazole,
5-chloro-1-(o-chlorophenyl)-3-(α,α,α-trifluoro-o-tolyl)-1H-1,2,4-triazole,
3-(o-ethylphenyl)-5-chloro-1-(o-methoxyphenyl)-1H-1,2,4-triazole,
1-(2-ethoxy-m-tolyl)-5-chloro-3-(o-chlorophenyl)-1H-1,2,4-triazole,
1-(o-bromophenyl)-5-chloro-3-(o-chlorophenyl)-1H-1,2,4-triazole,
5-chloro-3-(o-chlorophenyl)-1-(3-chloro-2,4-difluorophenyl)-1H-1,2,4-triazole,
5-chloro-3-(o-chlorophenyl)-1-(o-trifluoromethoxyphenyl)-1H-1,2,4-triazole,
5-chloro-3-(o-chlorophenyl)-1-(p-trifluoromethoxyphenyl)-1H-1,2,4-triazole,
5-chloro-3-(o-chlorophenyl)-1-(3,5-dichloro-4-trifluoromethoxyphenyl)-1H-1,2,4-triazole,
5-chloro-3-(o-chlorophenyl)-1-(3,5-dichloro-o-tolyl)-1H-1,2,4-triazole,
5-chloro-3-(o-chlorophenyl)-1-[3,5-di(trifluoromethyl)phenyl]-1H-1,2,4-triazole,
5-chloro-3-(o-chlorophenyl)-1-(α,α,α-trifluoro-m-tolyl)-1H-1,2,4-triazole,
5-chloro-3-(o-chlorophenyl)-1-(3-chloro-4-trifluoromethylphenyl)-1H-1,2,4-triazole,
5-chloro-3-(o-chlorophenyl)-1-(2-chloro-p-tolyl)-1H-1,2,4-triazole,
5-chloro-3-(o-chlorophenyl)-1-(3-nitro-o-tolyl)-1H-1,2,4-triazole,
5-chloro-1-(2,3-dichlorophenyl)-3-(2,6-difluorophenyl)-1H-1,2,4-triazole,
5-chloro-3-(2,6-difluorophenyl)-1-(p-trifluoromethoxyphenyl)-1H-1,2,4-triazole,
5-chloro-1-[3,5-dichloro-4-(1,1,2,2-tetrafluoroethoxy)phenyl]-3-(2,6-difluorophenyl)-1H-1,2,4-triazole,
5-chloro-3-(2,6-difluorophenyl)-1-(4-fluoro-3-trifluoromethylphenyl)-1H-1,2,4-triazole,
5-chloro-1-(4-chloro-3-trifluoromethylphenyl)-3-(2,6-difluorophenyl)-1H-1,2,4-triazole,
5-chloro-3-(2,6-difluorophenyl)-1-(p-trifluoromethylphenyl)-1H-1,2,4-triazole,
5-chloro-1-(3-chloro-4-trifluoromethylphenyl)-3-(2,6-difluorophenyl)-1H-1,2,4-triazole,
5-chloro-3-(2,6-difluorophenyl)-1-(5-fluoro-o-tolyl)-1H-1,2,4-triazole,
1-(3-chloro-o-tolyl)-3-(2,6-difluorophenyl)-5-fluoro-1H-1,2,4-triazole,
1-(3-chloro-o-tolyl)-3-(2,6-difluorophenyl)-5-methyl-1H-1,2,4-triazole,
3-(2,6-difluorophenyl)-1-(2,3-dimethylphenyl)-5-methyl-1H-1,2,4-triazole,
5-chloro-3-(2,6-dichlorophenyl)-1-phenyl-1H-1,2,4-triazole,
5-chloro-3-(2,6-dichlorophenyl)-1-(o-trifluoromethylphenyl)-1H-1,2,4-triazole,
5-chloro-3-(2,6-dichlorophenyl)-1-(o-tolyl)-1H-1,2,4-triazole,
5-chloro-3-(2-chloro-5-fluorophenyl)-1-(o-trifluoromethylphenyl)-1H-1,2,4-triazole,
5-chloro-1-(o-chlorophenyl)-3-(2-chloro-3-fluorophenyl)-1H-1,2,4-triazole,
5-chloro-3-(2,4-dichlorophenyl)-1-(o-trifluoromethylphenyl)-1H-1,2,4-triazole and
5-chloro-3-(o-chlorophenyl)-1-(4-chloro-2-trifluoromethylphenyl)-1H-1,2,4-triazole.

The compounds of the invention are prepared by the processes described as follows:

(a) for the preparation of those compounds of formula I in which $R^3$ is chlorine or bromine, treating a 1,4-dihydro-1H-1,2,4-triazol-5-one of the formula

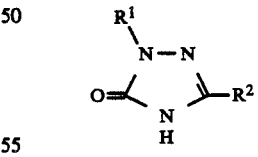

II wherein $R^1$ and $R^2$ are as defined above, with a chlorinating or brominating agent, (b) for the preparation of those compounds of formula I in which $R^3$ is fluorine or iodine, subjecting a 5-chloro-1,2,4-triazole of the formula

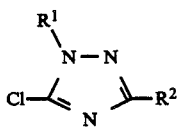

I' wherein $R^1$ and $R^2$ are as defined above, to a halogen exchange reaction, (c) for the preparation of those compounds of formula I in which $R^3$ is methyl or halomethyl, reacting a N-acylbenzimidic acid (thiol)ester or a N-acyl-benzimidamide of the formula

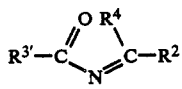   III wherein
$R^{3'}$ is methyl or halomethyl and
$R^4$ is lower alkoxy, lower alkylthio or di(lower alkyl)-amino and
$R^2$ is as defined above,
with a phenylhydrazine of the formula

   IV wherein $R^1$ is as defined above,
or with an acid addition salt thereof, or (d) for the preparation of those compounds of formula I in which $R^3$ is methyl or halomethyl, reacting an amidrazone of the formula

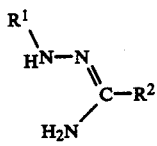   V wherein $R^1$ and $R^2$ are as defined above,
or an acid addition salt thereof with a carboxylic acid of the formula

   VI wherein $R^{3'}$ is as defined above,
or with a reactive derivative thereof.
and, if desired, converting a thus-obtained compound of formula I into the corresponding acid addition salt by reaction with an acid.

In the chlorination or bromination according to process variant (a) thionyl chloride, phosphorus pentachloride or phosphorus oxychloride, or phosphorus pentabromide or phosphoryl bromide, respectively, is conveniently used as the halogenating agent. If desired, a mixture of phosphorus pentachloride and phosphorus oxychloride or of phosphorus pentabromide and phosphoryl bromide is used, in which case an excess of phorphorus oxychloride or phosphoryl bromide can serve as the diluent. The chlorination or bromination can be carried out in the presence of an inert diluent, especially an aprotic organic solvent such as aliphatic or aromatic hydrocarbon, e.g. n-hexane, benzene, toluene or a xylene; a halogenated aliphatic hydrocarbon, e.g. methylene chloride, chloroform or 1,2-dichloroethane; a halogenated aromatic hydrocarbon, e.g. chlorobenzene or a tertiary amine, e.g. N,N-dimethylaniline, but this is not necessary when phosphorus oxychloride or phosphoryl bromide is used as the halogenating agent. When thionyl chloride is used as the halogenating agent, it has been found to be convenient to add a catalytic amount of dimethylformamide. The reaction temperature is generally between 0° C. and the reflux temperature of the reaction mixture, which is preferably from 80° C. to 120° C.

The halogen exchange reaction of process variant (b) is preferably effected by treating the 5-chloro-1,2,4-triazole of formula I' with an alkali metal or alkaline earth metal fluoride or iodide, the terms "alkali metal" and "alkaline earth metal" embracing especially sodium and potassium and calcium and magnesium respectively. The reaction is conveniently carried out by treating the 5-chloro-1,2,4-triazole with the alkali metal or alkaline earth metal fluoride or iodide in the presence of an inert diluent and—in the case of the fluorine exchange reaction—optionally with the addition of a phase transfer catalyst such as 18-crown-6 (the polyethylene ether crown compound with an 18-membered ring containing 6 oxygen atoms). As diluents for the fluorine exchange reaction there are especially suitable aliphatic ketones, e.g. 2-butanone; aromatics, e.g. toluene; aliphatic nitriles, e.g. acetonitrile; and aliphatic sulfones, e.g. sulfolane, while as diluents for the iodine exchange reaction there come in to consideration, in particular, also aliphatic ketones, e.g. 2-butanone as well as dimethylformamide. The reaction is conveniently effected at temperatures between about 20° C. and the reflux temperature of the reaction mixture.

In the case of process variant (c) there is to be understood under "lower alkoxy", "lower alkylthio" or "di(-lower alkyl)-amino" ($R^4$) such a group in which the alkyl part or each alkyl part contains especially 1 to 6 carbon atoms, but is preferably methyl or ethyl. Methoxy and ethoxy are the preferred leaving groups $R^4$. The acid addition salts of the phenylhydrazines of formula IV include the salts of these compounds formed with mineral acids, e.g. hydrochloric acid and hydrobromic acid, as well as organic acids, e.g. oxalic acid. However, the phenylhydrazine is preferably used in the form of the free base.

The reaction according to process variant (c) is conveniently effected in an inert diluent such as a chlorinated aliphatic or aromatic hydrocarbon, e.g. carbon tetrachloride, 1,1,2-trichloroethane or 1,2-dichlorobenzene; an alcohol, e.g. ethanol or 2-methoxyethanol; an aliphatic or cyclic ether, e.g. diethylene glycol diethyl ether, tetrahydrofuran or dioxan; an aliphatic nitrile, e.g. acetonitrile; an aliphatic or aromatic hydrocarbon, e.g. n-heptane, toluene or o- or p-xylene; or dimethylformamide. When a mineral salt or an organic salt of the phenylhydrazine of formula IV is used, the reaction is preferably also carried out in the presence of an acid-binding agent, e.g. triethylamine, 6-ethyl-2-methylpyridine, 2,6-lutidine or sodium acetate. The reaction temperatures can be varied in a wide range, the reaction being generally carried out at temperatures between 20° C. and the reflux temperature of the reaction mixture, which is preferably from 80° C. to 120° C.

Under certain circumstances in the case of process variant (c) there initially takes place, depending on the reaction conditions, only a hydrazine addition reaction with the formation of a compound of the isomeric formulae

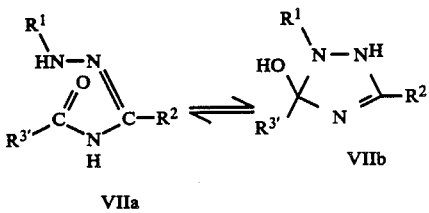

VIIa ⇌ VIIb

The compound VIIa⇌VIIb can, after isolation, be converted by heating to about 140°-220° C. (in the melt) with cleavage of water into the corresponding 5-methyl- or 5-halomethyl-1,2,4-triazole of the formula

I″

As an alternative to the further treatment of the compound VIIa⇌VIIb, they can, after isolation, be converted into the 1,2,4-triazole of formula I″ by treatment with a dehydrating agent such as phosphorus oxychloride or acetic anhydride in the presence of a diluent such as an aromatic, e.g. toluene.

In process variant (d) the carboxylic acid of formula VI or a reactive derivative thereof is firstly amidated with the amidrazone of formula V and thereupon cyclized. As reactive derivatives of the carboxylic acid of formula VI there come into consideration especially the acid halides such as the acid fluoride, the acid chloride and the acid bromide; the acid anhydride; an ortho ester of formula VIII, e.g. triethyl orthoacetate; and a N,N-dimethyl-carboxylic acid amide dialkyl acetal of formula IX, e.g. N-N-dimethylacetamide dimethyl acetal:

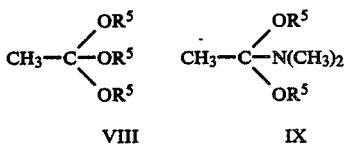

VIII    IX wherein $R^5$ is $C_{1-3}$-alkyl, especially methyl or ethyl. Examples of acid addition salts of the amidrazones of formula V are the hydrochloride, the hydrobromide and the oxalate.

The reaction according to this process variant is conveniently effected in the presence of an inert diluent and—when a carboxylic acid of formula VI, a halide thereof or an acid addition salt of the amidrazone of formula V is used—also in the presence of an acid-binding agent. When the acid anhydride of the carboxylic acid is used, the presence of an acid-binding agent is not necessary. As diluents there are suitable especially the diluents mentioned above in connection with process variant (c) as well as pyridine. As the acid-binding agent there is preferably used a tertiary amine such as triethylamine or pyridine or an organic salt such as potassium bicarbonate. If the reaction is effected using a carboxylic acid or its anhydride then an excess amount of the acid or of its anhydride can itself be used as the diluent in place of an added diluent. In any case, the reaction temperatures are generally between 0° C. and the reflux temperature of the reaction mixture.

A compound of formula I in which $R^3$ is methyl is prepared when the ortho ester of formula VIII or the N,N-dimethyl-carboxylic acid amide dialkyl acetal of formula IX is used. The corresponding reactant is conveniently used in excess. The reaction is effected by heating to about 100°-130° C., the corresponding alcohol $R^5OH$ being liberated. This alcohol is conveniently removed from the reaction mixture by distillation. For the manufacture of those compounds of formula I in which $R^3$ is methyl it is, however, especially preferred to react acetic anhydride with the amidrazone of formula V.

For the preparation of the acid addition salts of the compounds of formula I the compounds of formula I are reacted with the desired acids in the usual manner, for example by dissolving the compound of formula I in a suitable solvent such as diethyl ether, ethanol, ethyl acetate, toluene or methylene chloride and adding thereto the acid such as hydrogen chloride in the form of concentrated or gaseous hydrochloric acid. The resulting precipitate of the acid addition salt can subsequently be separated e.g. by filtration.

The isolation and the purification of the compounds of formula I or their acid addition salts, as above prepared, can be effected according to methods well-known in the art. For example, the compound of formula I can be isolated in the form of its acid addition salt and this can be treated with sodium hydroxide solution to liberate the free 1,2,4-triazole which, in turn, is purified by recrystallization, distillation or column chromatography.

The 1,4-dihydro-1H-1,2,4-triazol-5-ones of formula II which are used as starting materials in process variant (a) are novel and can be produced, for example, by reacting a lower alkyl chloroformate of the formula

   X wherein $R^6$ is lower alkoxy, with a benzimidic acid (thiol)alkyl ester or benzimidic acid di(lower alkyl)amide of the formula

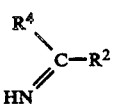   XI wherein $R^2$ and $R^4$ are as defined above, and reacting the thus-produced N-alkoxycarbonyl-benzimidic acid (thiol)ester or the thus-produced N-alkoxycarbonyl-benzimidamide of the formula

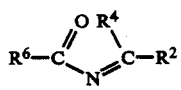   XII wherein $R^2$, $R^4$ and $R^6$ are as defined above, with a phenylhydrazine of formula IV given above or with an acid addition salt thereof.

The reaction of the compound of formula X with the compound of formula XI is conveniently effected in the presence of a base, especially a sterically hindered base such as 2,6-lutidine or sym-collidine, as well as in the presence of an inert diluent such as a hydrocarbon, e.g. n-hexane or petrol, at elevated temperature, e.g. at the reflux temperature of the reaction mixture. This production procedure is exemplified, for example, in *Syn-* thesis 1983, 483–6. The lower alkoxy group $R^6$ which is present in the starting material of formula X is especially a $C_{1-6}$-alkoxy group, preferably methoxy or ethoxy.

The subsequent reaction of the compound of formula XII produced in the first step with the phenylhydrazine of formula IV or with an acid addition salt thereof is conveniently carried out under the reaction conditions which are described above in connection with process variant (c). Here again the acid addition salts of the phenylhydrazines of formula IV include the salts formed with mineral acids, e.g. hydrochloric acid and hydrobromic acid, as well as organic acids, e.g. oxalic acid. However, the phenylhydrazine is preferably used in the form of the free base. Under certain circumstances there initially takes place, depending on the reaction conditions, only a hydrazine addition reaction with the formation of a compound of the isomeric formulae

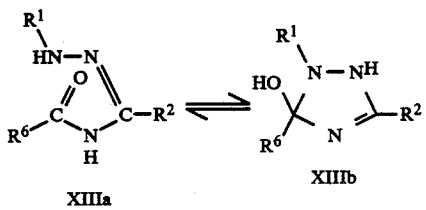

The compound XIIIa⇌XIIIb can, after isolation, be converted by heating to about 140°–220° C. (in the melt) with cleavage of the lower alkanol $R^6OH$ into the corresponding 1,4- or 1,2-dihydro-1H-1,2,4-triazol-5-one of formula II or II'

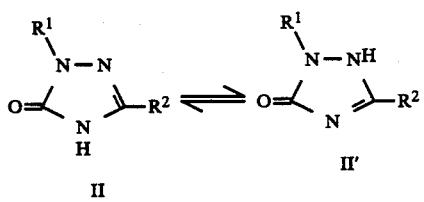

The isolation of the compound II⇌II' is, however, not essential: the reaction of the N-alkoxycarbonyl-benzimidic acid (thiol)ester or -benzimidamide of formula XII with the phenylhydrazine of formula IV is conveniently effected initially in an optionally chlorinated aromatic hydrocarbon such as toluene or 1,2-dichlorobenzene at temperatures between 20° C. and 80° C., and the mixture is subsequently heated to about 110°–160° C. for the cyclization and water-cleavage of the compound XIIIa⇌XIIIb which is formed in situ. The alkanol $R^6H$ which is formed is conveniently distilled off azeotropically from the reaction mixture.

The 1,4-dihydro-1H-1,2,4-triazol-5-ones of formula II can also be produced, for example, by treating an amidrazone of formula V given above or acid addition salt thereof with phosgene or a lower alkyl chloroformate, preferably a $C_{1-3}$-alkyl chloroformate. Examples of acid addition salts of the amidrazones of formula V are the hydrochloride, the hydrobromide and the oxalate.

The reaction is conveniently carried out in the presence of an inert diluent and using an acid-binding agent. As diluents there are especially suitable the diluents mentioned in the case of process variant (c) as well as pyridine. A tertiary amine such as triethylamine or pyridine is preferably used as the acid-binding agent. In carrying out this reaction the reaction temperatures can also be varied in a wide range, the reaction being conveniently carried out at temperatures between 0° C. and the reflux temperature of the reaction mixture.

The N-acylbenzimidic acid (thiol)esters and amides of formula III which are used as starting materials in process variant (c) are either known per se or can be produced by methods well-known in the art, for example by acylating a benzimidic acid (thiol)alkyl ester or benzimidic acid di(lower alkyl)amide of formula XI given above or an acid addition salt thereof, e.g. the hydrochloride or tetrafluoroborate salt, with a carboxylic acid of formula VI given above or with a reactive derivative thereof, conveniently under the reaction conditions given above in connection with process variant (d) (see also e.g. Synthesis 1983, 483-6).

The phenylhydrazines of formula IV and their acid addition salts which are used as starting materials of process variant (c) are also known or can be produced according to methods known per se, e.g. diazotization (see Houben-Wehl, Methoden der Organischen Chemie, Volume 10/2, page 180 et. seq.).

The amidrazones of formula V and their acid addition salts which are used as starting materials in process variant (d) and, moreover, for the production of the starting materials II, are also either known per se or can be produced according to methods well-known in the art, for example by reacting a phenylhydrazine of formula IV given above or an acid addition salt thereof, e.g. the hydrochloride salt, with an alkyl benzimidate of the formula

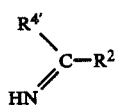

wherein
$R^2$ is as defined above and
$R^{4'}$ is lower alkoxy, preferably methoxy or ethoxy,
or with an acid addition salt thereof, e.g. the hydrochloride or tetrafluoroborate salt. The reaction is conveniently effected in an inert diluent such as a chlorinated aliphatic hydrocarbon, e.g. methylene chloride; an aromatic, e.g. toluene; an aliphatic or cyclic ether, e.g. tetrahydrofuran or dioxan; a lower alkanol, e.g. ethanol; or pyridine, at relatively low temperatures, e.g. between 0° C. and room temperature.

A further method for the production of these amidrazones comprises subjecting a N-phenyl-benzhydrazinoyl chloride of the formula

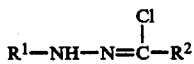

wherein $R^1$ and $R^2$ are as defined above,
to an aminolysis. For this purpose, a solution of the N-phenyl-benzhydrazinoyl chloride in an inert solvent such as an aromatic, e.g. toluene, or an ether, e.g. diethyl ether, is treated at about −40° C. to 20° C. with a solution of ammonia in ethanol or water or with gaseous ammonia.

This and further methods for the production of the amidraznes of formula V are described, inter alia, in

*Chemical Reviews* 70, 151–170 (1970) and in the literature cited therein.

The N-phenyl-benzhydrazinoyl chlorides of formula XIV are either known per se or can be produced according to methods well-known in the art, for example by firstly reacting a benzoyl chloride of the formula $$R^2COCl \qquad XV$$

wherein $R^2$ is as defined above, with a phenylhydrazine of formula IV given above or an acid addition salt thereof, e.g. the hydrochloride salt, and subsequently treating the thus-obtained N-phenyl-benzhydrazide of the formula $$R^1-NH-NH-CO-R^2 \qquad XVI$$

with a chlorinating agent such as thionyl chloride, phosphorus pentachloride or phosphorus oxychloride. Both reaction steps can be carried out under the conditions which are familiar to the person skilled in the art.

The 1,2,4-triazoles of formula I' which are used as starting materials in process variant (b) are a sub-group of the compounds of formula I and can be produced in accordance with process variant (a).

The remainder of the above-mentioned starting materials, intermediates or reagents, thus, inter alia, the compounds of formulae VI (and their reactive derivatives e.g. the compounds of formulae VIII and IX), X, XI and XV, are also either known per se or can be produced according to methods known in the art. The isolation and the purification of these starting materials can also be carried out according to well-known methods.

The compounds in accordance with the invention, i.e. the compounds of formula I and their acid addition salts, are quite generally of value as pesticides. They have been found to be particularly valuable for the control of insects and mites, especially of Homoptera (especially aphids) such as e.g. *Aphis fabae, Aphis gossypii, Aphis pomi; Acyrthosiphon pisum, Acyrthosiphon dirhodum; Brevicoryne brassicae; Dysaphis devecta, Dysaphis pyri, Dysaphis plantaginea; Macrosiphum rosae; Macrosiphum avenae; Myzus persicae, Myzus cerasi; Phorodon humuli; Rhopalosiphum insertum, Rhopalsiphum padi; Toxoptera aurantii; Nasonovia ribisnigri; Hyalopterus pruni;* leaf lice (Psyllina) such as *Psylla piri, Psylla pirisuga, Psylla piricola, Psylla mali;* white flies such as e.g. *Trialeurodes vaporariorum; Aleurothrixus floccosus; Bemisia tabaci; Aleurodes proletella; Aleurocanthus woglumi; Dialeurodes citri;* mites which are of importance in plant protection such as e.g. Tetranychidae (spider mites), especially *Tetranychus urticae, Tetranychus cinnabarinus, Tetranychus turkestani, Tetranychus McDanieli, Tetranychus kanzawai; Panonychus ulmi, Panonychus citri; Phyllocoptruta oleivora; Aculus schlechtendali; Phyllocoptes vitis; Aceria essigi, Aceria gracilis; Cecidophyopsis ribis; Eriophyes vitis; Eotetranychus sexmaculatus, Eotetranychus carpini; Hemitarsonemus latus;* mites which are of importance in veterinary medicine such as e.g. *Macronyssus bursa, Macronyssus sylviarum, Macronyssus lacoti; Dermanyssus gallinae;* ticks, especially of the families Ixodidae and Argasidae and of the orders Boophilus, Amblyomma, Hyalomma, Rhipicephalus, Ixodes, Argas and Ornithodorus.

The compounds in accordance with the invention act as contact and feed poisons. Moreover, some of the compounds are taken up by various plants, so that the pests to be controlled are killed when they eat the plants. These compounds thus exhibit systemic activity.

The pest control composition in accordance with the invention contains an effective amount of at least one compound of general formula I, as defined above, or an acid addition salt of such a compound as well as formulation adjuvants. The composition conveniently contains at least one of the following formulation adjuvants:

Solid carrier substances; solvents or dispersion media; tensides (wetting and emulsifying agents); dispersing agents (without tenside action); and stabilizers.

With the use of these and additional adjuvants the compounds of formula I, or their acid addition salts, namely the pesticidally active substances, can be converted into the usual formulations such as solutions, suspensions, emulsions, emulsifiable concentrates, pastes, foams, dusts, powders and granulates.

As solid carrier substances there may be used: natural mineral substances such as kaolin, aluminas, siliceous earth, talc, bentonite, chalk, limestone, quartz, dolomite, attapulgite, montmorillonite and diatomaceous earth; synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as dusts, powders or granulates.

As solvents or dispersion media there may be used: aromatics such as toluene, xylenes, benzene and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol as well as their ethers and esters; ketones such as acetone, methyl isobutyl ketone and cyclohexanone; and stongly polar solvents such as dimethylformamide, N-methylpyrrolidone and dimethyl sulfoxide, such solvents or dispersion media preferably having flash points of at least 30° C. and boiling points of at least 50° C., and water. Among the solvents or dispersion media there may also be used the so-called liquified gaseous extenders or carrier substances, these being products which are gaseous at room temperature and under normal pressure. Examples of such products are especially aerosol propellants such as halogenated hydrocarbons, e.g. dichlorodifluoromethane. When water is used as the solvent, organic solvents can also be used as auxiliary solvents.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulfate, octadecyl sodium sulfate and cetyl sodium sulfate; alkyl sulfonates, aryl sulfonates and fatty-aromatic sulfonates such as alkylbenzenesulfonates, e.g. calcium dodecylbenzenesulfonate, and butylnaphthalenesulfonates; and more complex fatty sulfonates, e.g. the amide condensation products of oleic acid and N-methyltaurine and the sodium sulfonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there may be used lignin, sodium and ammonium salts of lignin sulfonic acids, sodium slats of maleic anhydride-diisobutylene copolymers, sodium and ammonium salts of sulfonated polycondensation products from naphthalene and formaldehyde, and sulfite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents e.g. epichlorohydrin, phenyl glycidyl ether and soya epoxides; antioxidants e.g. gallic acid esters and butylhydroxytoluene; UV-absorbers e.g. substituted benzophenones, diphenylacrylonitrile acid esters and cinnamic acid esters; and deactivators e.g. salts of ethylenediaminotetraacetic acid and polyglycols.

The pest control compositions in accordance with the invention can contain, in addition to the active substances of formula I, other active substances, e.g. other pest control agents, pest baits, fungicides, bactericides, herbicides, plant growth regulators and fertilizers. Such combination compositions are suitable for intensifying the activity or for broadening the spectrum of activity. If desired, insufficiencies of hitherto known added agents can thereby also be compensated for.

It has been found that the compounds in accordance with the invention, especially those indicated hereinbefore as being especially preferred, can be used with advantage in combination with other acaricides, primarily with acaricides which are suitable for the control of mobile stages of mites. Examples of such acaricides are amitraz, avermectin, benzoximate, bromopropylate, chlorobenzilate, cyhexatin, dicofol, fenbutatin oxide, methidathion, propargite and ethyl 5,7-dihydro-6H-dibenz[c,e]azepine-6-carboximidate as well as pyrethroids having acaricidal activity such as, for example fluvalinate, biphenthrin and cyano-3-phenoxybenzyl-3-(2-chloro-2,3,3-trifluoroprop-1-enyl)-2,2-dimethyl-cyclopropane carboxylate. The use can be carried out simultaneously as a mixture or separately. Thereby, the active substances in accordance with the invention can compensate for the disadvantage of the known acaricides having a main focus of activity against adult pests, in that the eggs and larvae which survive after the use of the known acaricides and which can develop rapidly into a new pest population are also killed by the compounds of the present invention.

The pest control compositions in accordance with the invention generally contain between 0.005 and 95 weight percent of the compound(s) of formula I in accordance with the invention as the active substance(s). They can be present in a form which is suitable for storage and transport. In such forms, e.g. emulsifiable concentrates, the active substance concentration is normally in the higher region of the above concentration range. These forms can be diluted with the same or different formulation adjuvants to give active substance concentrations which are suitable for practical use and such concentrations normally lie in the lower region of the above concentration range. Emulsifiable concentrates generally contain 5 to 95 weight percent, preferably 10 to 80 weight percent, of the compound(s) in accordance with the invention. As forms of use there may be used, inter alia, ready-for-use solutions, emulsions, suspensions, foams, powders, pastes, dusting compositions and granulates. The active substance concentrations in such ready-for-use compositions can be varied in wide limits. In spray liquors there can be present e.g. concentrations between 0.005 and 0.5 weight percent. In the Ultra-Low-Volume process there can be formulated spray liquors in which the active substance concentration is preferably from 10 to 20 weight percent, while the spray liquors formulated in the Low-Volume process and in the High-Volume process preferably have an active substance concentration of 0.01 to 0.5 and 0.005 to 0.1 weight percent, respectively. Granulates preferably contain from 5 to 50 weight percent of the compound(s) in accordance with the invention as the active substance.

The pest control compositions in accordance with the invention can be manufactured by mixing at least one compound of general formula I or an acid addition salt of such a compound with formulation adjuvants.

The manufacture of the compositions can be carried out in a known manner, e.g. by mixing the active substance with solid carrier substances, by dissolution or suspension in suitable solvents or dispersion media, if necessary using tensides as wetting or emulsifing agents, or dispersing agents, by diluting pre-prepared emulsifiable concentrates with solvents or dispersion media, etc.

In the case of pulverous compositions the active substance can be mixed with a solid carrier substance, e.g. by grinding together; or the solid carrier substance can be impregnated with a solution or suspension of the active substance and then the solvent or suspension medium can be removed by evaporation, by heating or by sucking-off under reduced pressure. By adding tensides or dispersing agents such pulverous compositions can be made readily wettable with water, so that they can be converted into aqueous suspensions which are suitable e.g. as spray compositions.

The compounds of formula I or their acid addition salts can also be mixed with a tenside and a solid carrier substance to form a wettable powder which is dispersible in water or they can be mixed with a solid pre-granulated carrier substance to form a product in the form of a granulate.

If desired, the compound of formula I or an acid addition salt thereof can be dissolved in a water-immiscible solvent such as, for example, an alicyclic ketone, which conveniently contains a dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The method in accordance with the invention for the control of pests comprises treating the locus to be protected or the pests themselves with an effective amount of a compound in accordance with the invention or of a pest control composition in accordance with the invention. This method of use can be carried out by application to the soil or leaves or by application to the animals, supplies or materials to be protected, depending on the kind of pests to be controlled. The control is achieved, for example, by contact or by intake with the feed.

The use can be carried out in a conventional manner, e.g. by sprinkling, spraying, atomising, dusting, scattering, drilling-in, smoking, watering, steeping or coating. Pulverous preparations can be applied to the pests or to the locus to be protected, e.g. plants or animals, as e.g. dusting agents with the aid of the usual dusting appliances. Aqueous suspensions can be used e.g. as spray compositions.

When used in plant protection a dosage of about 120–500 g of active substance [compound(s) of formula I]/ha, is usually sufficient, e.g. as is the case in the application of 2000 l of a spray liquor which contains 0.006–0.025 weight percent of active substance to 1 ha of cultivated land.

The following Examples illustrate the invention.

I. Preparation of the compounds of formula I

EXAMPLE 1

A mixture of 9.8 g (32 mmol) of 1,3-bis-(o-chlorophenyl)-1,4-dihydro-1H-1,2,4-triazol-5-one and 7.3 g (35 mmol) of phosphorus pentachloride in 20 ml of phorphorus oxychloride is heated at 110° C. for 24 hours. Thereafter a further 2.97 g (14 mmol) of phosphorus pentachloride are added thereto and the mixture is heated at reflux temperature for a further 22 hours. The cooled reaction mixture is cautiously added dropwise to water at 30°–35° C. while controlling the temperature and the aqueous mixture is neutralized with 30% sodium hydroxide solution and extracted twice with 150 ml of diethyl ether. The combined extracts are washed once with saturated sodium chloride solution, dried over anhydrous magnesium sulfate and evaporated under reduced pressure. By eluting the residue with n-hexane/ethyl acetate (17:3) on silica gel (0 40–63 μm) and subsequent recrystallization from ethyl acetate/n-hexane there is obtained a pure product, namely 1,3-bis-(o-chlorophenyl)-5-chloro-1H-1,2,4-triazole, m.p. 95.5° C.; mass spectrum: 323(66), 262(24), 125(100).

The 1,3-bis-(o-chlorophenyl)-5-chloro-1H-1,2,4-triazole can also be manufactured as follows:

A suspension of 13.7 g (45 mmol) of 1,3-bis-(o-chlorophenyl)-1,4-dihydro-1H-1,2,4-triazol-5-one in 40 ml (0.44 mol) of phosphorus oxychloride is heated at reflux temperature for 24 hours. The reaction mixture, which has become clear, is then cautiously added dropwise to water at 30°–35° C. while controlling the temperature. The mixture is subsequently neutralized with 28% sodium hydroxide solution and extracted twice with 150 ml of diethyl ether each time. The combined extracts are washed with saturated sodium chloride solution, dried over anhydrous magneisum sulfate and evaporated under reduced pressure. After distillation of the residue in a bulb-tube at 175° C./0.1 mmHg (13.33 Pa) there is obtained pure 1,3-bis-(o-chlorophenyl)-5-chloro-1H-1,2,4-triazole, m.p. 95.5° C.; mass spectrum: 323(35), 262(14), 125(100).

EXAMPLES 2-36

The corresponding 1,4-dihydro-1H-1,2,4-triazol-5-ones of formula II are chlorinated or brominated analogously to the procedure described in Example 1 in order to manufacture the compounds of formula I listed in Table 1 hereinafter.

TABLE 1

| Example | R$^1$ | R$^2$ | R$^3$ | Physical data |
|---|---|---|---|---|
| 2 | α,α,α-Trifluoro-o-tolyl | o-Chlorophenyl | Chloro | B.p. 160° C./0.05 mmHg (6.67 Pa); mass spectrum: 357(80), 296(37), 159(100) |
| 3 | " | 2,6-Difluorophenyl | " | M.p. 100–100.5° C. Mass spectrum: 359(69), 298(57), 159(100) |
| 4 | o-Chlorophenyl | 2-Chloro-4-fluorophenyl | " | M.p. 103.5° C. Mass spectrum: 341(16), 280(5), 125(100) |
| 5 | " | 2,6-Difluorophenyl | " | M.p. 94° C. Mass spectrum: 325(10), 264(5), 125(100) |
| 6 | α,α,α-Trifluoro-o-tolyl | 2-Chloro-4-fluorophenyl | " | M.p. 87° C. Mass spectrum: 375(45), 314(17), 159(100) |
| 7 | " | 2-Chloro-6-fluorophenyl | " | M.p. 76° C. Mass spectrum: 375(48), 314(41), 159(100) |
| 8 | o-Chlorophenyl | " | " | M.p. 85° C. Mass spectrum: 341(22), 280(11), 125(100) |
| 9 | 3,4-Dichlorophenyl | 2,6-Difluorophenyl | Chloro | M.p. 143.5° C. Mass spectrum: 359(39), 298(15), 159(100) |
| 10 | o-Tolyl | o-Chlorophenyl | " | B.p. 165° C./0.06 mmHg (8.00 Pa) Mass spectrum: 303(1/), 268(100), 131(48) |
| 11 | α,α,α-Trifluoro-o-tolyl | o-Iodophenyl | " | B.p. 210° C./0.05 mmHg (6.67 Pa) Mass spectrum: 449(100), 388(18), 159(40) |
| 12 | 2-Chloro-6-methylphenyl | o-Chlorophenyl | " | M.p. 76° C. Mass spectrum: 337(30), 302(100) |
| 13 | 4-Chloro-o-tolyl | " | " | M.p. 70.5° C. Mass spectrum: 337(24), 302(99) |

TABLE 1-continued

| Example | R¹ | R² | R³ | Physical data |
|---|---|---|---|---|
| 14 | 3-Chloro-o-tolyl | " | " | B.p. 175° C./0.06 mmHg (8.00 Pa) Mass spectrum: 337(26), 302(100) |
| 15 | 5-Chloro-o-tolyl | " | " | M.p. 89° C. Mass spectrum: 337(29), 302(100) |
| 16 | 2-Chloro-5-trifluoromethylphenyl | o-Chlorophenyl | Chloro | B.p. 175° C./0.08 mmHg (10.67 Pa) Mass spectrum: 391(53), 330(20), 193(100) |
| 17 | 2-Chloro-6-fluorophenyl | " | " | M.p. 88–89° C. Mass spectrum: 341(42), 280(10), 143(100) |
| 18 | o-Tolyl | 2,6-Difluorophenyl | " | B.p. 180° C./0.055 mmHg (7.34 Pa) Mass spectrum: 305(18), 270(100), 131(47) |
| 19 | Phenyl | " | " | M.p. 59° C. Mass spectrum: 291(35), 230(14), 91(100) |
| 20 | 3,5-Dichlorophenyl | " | " | M.p. 121° C. Mass spectrum: 359(72), 298(46), 159(100) |
| 21 | 2,4-Dimethylphenyl | " | " | B.p. 150° C./0.05 mmHg (6.67 Pa); $^1$H—NMR (CDCl$_3$, 60 MHz): 2.19 (s, C$\underline{H}_3$), 2.41 (s, C$\underline{H}_3$) Mass spectrum: 319(23), 284(100), 145(41) |
| 22 | Phenyl | o-Chlorophenyl | Chloro | M.p. 86° C. Mass spectrum: 289(39), 228(13), 91(100) |
| 23 | α,α,α-Trifluoro-m-tolyl | 2,6-Dimethoxyphenyl | " | M.p. 170–172° C. $^1$H—NMR (CDCl$_3$, 60 MHz): 3.81 (s,2 × OC$\underline{H}_3$); Mass spectrum: 383(70) |
| 24 | " | 2,6-Difluorophenyl | " | M.p. 77–79° C. Mass spectrum: 359(46), 298(34), 159(100) |
| 25 | 3-Chloro-o-tolyl | " | " | M.p. 100–102° C. $^1$H—NMR (CDCl$_3$, 60 MHz): 2.22 (s, C$\underline{H}_3$) Mass spectrum: 339(25), 304(100) |
| 26 | " | 2-Chloro-6-fluorophenyl | " | M.p. 74–76° C. $^1$H—NMR (CDCl$_3$, 60 MHz): 2.24 (s, C$\underline{H}_3$) Mass spectrum: 357(21), 320(100) |
| 27 | 2,3-Dimethylphenyl | o-Chlorophenyl | " | M.p. 69° C. $^1$H—NMR (CDCl$_3$, 60 MHz): 2.09 (s, C$\underline{H}_3$), 2.39 (s, C$\underline{H}_3$) |
| 28 | 2,3-Dimethylphenyl | 2,6-Difluorophenyl | Chloro | M.p. 105° C. $^1$H—NMR (CDCl$_3$, 60 MHz): 2.04 (s, C$\underline{H}_3$), 2.37 (s, C$\underline{H}_3$); Mass spectrum: 319(21), 284(100) |
| 29 | m-Fluorophenyl | o-Chlorophenyl | " | M.p. 73° C. Mass spectrum: 307(66), 246(50), 109(100) |
| 30 | o-Nitrophenyl | " | " | M.p. 102° C. Mass spectrum: 335(17) |
| 31 | o-Bromophenyl | 2,6-Difluorophenyl | " | M.p. 99–100° C. Mass spectrum: 369/371 (52), 308/310(9), 90(100) |
| 32 | o-Methoxyphenyl | o-Chlorophenyl | " | Oil $^1$H—NMR (CDCl$_3$, 60 MHz): 3.87 (s,OC$\underline{H}_3$); Mass spectrum: 319(21), 284(100) |
| 33 | o-Fluorophenyl | " | " | M.p. 70–72° C. Mass spectrum: 307(32), 246(12), 109(100) |
| 34 | 3-Chloro-2-cyanophenyl | o-Chlorophenyl | Chloro | M.p. 174–175° C. Mass spectrum: 348(97), |

TABLE 1-continued

| Example | R[1] | R[2] | R[3] | Physical data |
|---|---|---|---|---|
| 35 | o-Cyanophenyl | 2,6-Difluoro-phenyl | " | 287(12), 150(100) M.p. 155° C. IR: 2238 cm$^{-1}$; mass spectrum: 316(21), 297(14), 255(25), 116(100) |
| 36 | α,α,α-Trifluoro-o-tolyl | " | Bromo | M.p. 73–74° C. Mass spectrum: 403/405 (46), 298(67), 159(100) |

EXAMPLE 37

A mixture of 2.61 g (6.9 mmol) of 5-chloro-3-(2-chloro-6-fluorophenyl)-1-(α,α,α-trifluoro-o-tolyl)-1H-1,2,4-triazole, 0.84 g (14.5 mmol) of dry potassium fluoride and 0.23 g (0.9 mmol) of 18-crown-6 in 15 ml of dry sulfolane is heated at 140° C. for 65 hours. The reaction mixture is subsequently cooled and eluted on silica gel (φ 40–63 μm, column: 0 7 cm, height 20 cm) with ethyl acetate/n-hexane (7:13). There is obtained 3-(2-chloro-6-fluorophenyl)-5-fluoro-1-(α,α,α-trifluoro-o-tolyl)-1H-1,2,4-triazole as white crystals, m.p. 68°–70° C.; mass spectrum: 359(100).

EXAMPLE 38

A mixture of 11.3 g (50 mmol) of ethyl N-acetyl-o-chlorobenzimidate and 8.8 g (50 mmol) of o-trifluoromethylphenylhydrazine in 60 ml of carbon tetrachloride is heated at reflux temperature for 3 hours. The reaction mixture is then diluted with 240 ml of methylene chloride and the whole is washed with 100 ml of water. The organic phase is subsequently dried over anhydrous magnesium sulfate and evaporated under reduced pressure.

There are thus obtained 15.6 g of residue which is then taken up in 80 ml of toluene and heated at reflux temperature for 1 hours together with 4.6 ml (50 mmol) of phosphorus oxychloride. The mixture is subsequently taken up in 200 ml of diethyl ether and the solution is washed in each case once with 5% sodium bicarbonate solution and saturated sodium chloride solution, dried over anhydrous magnesium sulfate and evaporated under reduced pressure. The residue is purified by chromatography on silica gel (100 40–60 μm) with n-hexane/acetone (3:1) and subsequently subjected to a bulb-tube distillation, the fraction with b.p. 180° C./0.1 mmHg (13.33 Pa) being collected. In this manner there is obtained as a yellow-orange coloured oil 3-(o-chlorophenyl)-5-methyl-1-(α,α,α-trifluoro-o-tolyl)-1H-1,2,4-triazole, $^1$H—NMR (CDCl$_3$, 60 MHz): 2.38 (s,CH$_3$); mass spectrum; 337(46), 296(53), 159(100).

EXAMPLE 39

A mixture of 6.1 g (22 mmol) of ethyl N-acetyl-2-chloro-4-fluorobenzimidate and 6.7 g (25 mmol) of o-trifluoromethylphenylhydrazine hydrochloride in 100 ml of toluene is treated with 3.9 ml (28 mmol) of triethylamine and the whole is heated at reflux temperature for 18 hours. Thereafter, the reaction mixture is washed once with water and extracted twice with 50 ml of concentrated hydrochloric acid. The acidic aqueous phases are neutralized with ice-cold sodium hydroxide solution and extracted twice with diethyl ether, and the combined extracts are dried over anhydrous magnesium sulfate and evaporated under reduced pressure. The residue is subjected to a bulb-tube distillation, the fractions with b.p. 200° C./0.01 mmHg (9.33 Pa) being collected and finally crystallized from diisopropyl ether/n-hexane. In this manner there is obtained 3-(2-chloro-4-fluorophenyl)-5-methyl-1-(α,α,α-trifluoro-o-tolyl)-1H-1,2,4-triazole, m.p. 116° C.; $^1$H—NMR (CDCl$_3$, 60 MHz): 2.37 (s,CH$_3$); mass spectrum: 335(48), 314(43), 159(100).

EXAMPLES 40–54

The corresponding starting materials of formulae III and IV (free hydrazine or acid addition salt thereof) are reacted with one another analogously to the procedure described in Example 38 or 39 in order to manufacture the compounds of formula I listed in Table 2 hereinafter.

TABLE 2

| Example | R[1] | R[2] | R[3] | Physical data |
|---|---|---|---|---|
| 40 | α,α,α-Trifluoro-o-tolyl | o-Fluorophenyl | Methyl | B.p. 200° C./0.05 mmHg (6.67 Pa); $^1$H—NMR (CDCl$_3$, 60 MHz): 2.37 (s, CH$_3$) |
| 41 | " | 2,4-Dichloro-phenyl | " | M.p. 95–96° C. $^1$H—NMR (CDCl$_3$, 60 MHz): 2.42 (s, CH$_3$) Mass spectrum: 371(44), 330(44), 159(100) |
| 42 | " | o-Bromophenyl | " | M.p. 67–68.5° C. $^1$H—NMR (CDCl$_3$, 60 MHz): 2.38 (s, CH$_3$) Mass spectrum: 381/383(28), 340/342(22), 159(100) |
| 43 | " | o-Tolyl | " | Oil $^1$H—NMR (CDCl$_3$, 60 MHz): 2.37 (s, CH$_3$), 2.63 (s, CH$_3$) Mass spectrum: 317(100), 159(60) |
| 44 | " | o-Methoxyphenyl | " | B.p. 200° C./0.05 mmHg (6.67 Pa); $^1$H—NMR (CDCl$_3$, 60 MHz): |

TABLE 2-continued

| Example | R¹ | R² | R³ | Physical data |
|---|---|---|---|---|
| | | | | 2.35 (s, C$\underline{H}_3$), 3.91 (s, OC$\underline{H}_3$)<br>Mass spectrum: 333(41), 304(48), 262(28), 159(78) |
| 45 | 4-Bromo-2-tri-fluoromethyl-phenyl | o-Chlorophenyl | Methyl | M.p. 82–84° C.<br>¹H—NMR (CDCl₃, 60 MHz): 2.39 (s, C$\underline{H}_3$)<br>Mass spectrum: 415/417(54), 374/376(50), 237/239(100) |
| 46 | o-Fluorophenyl | " | " | M.p. 67° C.<br>¹H—NMR (CDCl₃, 60 MHz): 2.50 (d, J = 2Hz, C$\underline{H}_3$)<br>Mass spectrum: 287(28), 246(25), 109(100) |
| 47 | o-Bromophenyl | 2,6-Difluoro-phenyl | " | M.p. 125° C.<br>¹H—NMR (CDCl₃, 60 MHz): 2.45 (s, C$\underline{H}_3$)<br>Mass spectrum: 349/351(37), 308/310(27), 169/171(84) |
| 48 | o-Chlorophenyl | α,α,α-Trifluoro-o-tolyl | " | B.p. 175° C./0.03 mmHg (4.00 Pa); ¹H—NMR (CDCl₃, 60 MHz): 2.42 (s, C$\underline{H}_3$)<br>Mass spectrum: 337(29), 296(21), 125(100) |
| 49 | " | o-Chlorophenyl | Chloro-methyl | M.p. 98.5° C.<br>¹H—NMR (CDCl₃, 60 MHz): 4.63 (s, C$\underline{H}_2$Cl)<br>Mass spectrum: 339(31), 337(29), 262(30), 125(100) |
| 50 | o-Tolyl | 2,6-Difluoro-phenyl | Methyl | M.p. 97–98° C.<br>¹H—NMR (CDCl₃, 60 MHz): 217 (s, C$\underline{H}_3$), 2.44 (s, C$\underline{H}_3$)<br>Mass spectrum: 285(89), 270(34), 244(6), 105(100) |
| 51 | α,α,α-Trifluoro-o-tolyl | o-Iodophenyl | " | M.p. 71–73° C.<br>¹H—NMR (CDCl₃, 60 MHz): 2.39 (s, C$\underline{H}_3$)<br>Mass spectrum: 429(86), 388(42), 159(100) |
| 52 | α,α,α-Trifluoro-m-tolyl | 2,6-Difluoro-phenyl | " | ¹H—NMR (CDCl₃, 60 MHz): 2.68 (s, C$\underline{H}_3$)<br>Mass spectrum: 339(49), 298(50), 159(100) |
| 53 | Phenyl | " | " | B.p. 210° C./0.15 mmHg (20.00 Pa)<br>¹H—NMR (CDCl₃, 60 MHz): 2.64 (s, C$\underline{H}_3$)<br>Mass spectrum: 271(40), 230(31), 91(100) |
| 54 | o-Chlorophenyl | o-Chlorophenyl | " | M.p. 74–76° C.<br>¹H—NMR (CDCl₃, 60 MHz): 2.45 (s, C$\underline{H}_3$)<br>Mass spectrum: 337(29), 296(21), 125(100) |

EXAMPLE 55

A mixture of 5.1 g (23 mmol) of ethyl N-acetyl-o-chlorobenzimidate and 3.8 g (25 mmol) of o-nitrophenylhydrazine in 200 ml of tetrahydrofuran is heated at reflux temperature for 3 days. The solvent is then removed by evaporation, the residue is taken up in methylene chloride and the solution is washed with 5% sodium bicarbonate solution. The organic phase is dried over anhydrous magnesium sulfate and evaporated under reduced pressure. By eluting the residue with n-hexane/acetone (3:1) on silica gel (φ 40–63 μm) and subsequent crystallization there is obtained pure intermediate, namely N-acetyl-N'-(o-nitrophenylhydrazino)-o-chlorobenzimidic acid amide as an orange coloured crystallizate, m.p. 196°–198° C.

2.85 g (8.6 mmol) of the above intermediate and 1.1 ml (12 mmol) of phosphorus oxychloride are heated at reflux temperature in 15 ml of toluene for 2 hours. The mixture is subsequently taken up in 60 ml of ethyl acetate, the solution is extracted twice with 30 ml of concentrated hydrochloric acid, the acidic aqueous phases are adjusted to pH 2–3 with ice-cold sodium hydroxide solution and extracted twice with 60 ml of ethyl acetate. The combined extracts are washed in each case once with ice-cold dilute sodium hydroxide solution and saturated sodium chloride solution, dried over anhydrous sodium sulfate and evaporated under reduced pressure, and the residue is then taken up twice in hot acetone and the combine solutions are treated with active carbon and treated with n-hexane in order to precipitate the product. In this manner there is obtained 3-(o-chlorophenyl)-5-methyl-1-(o-nitrophenyl-1H-1,2,4-triazole as orange coloured crystals, m.p.

108°–109° C.; ¹H—NMR (CDCl₃, 60 MHz): 2,49 (s,CH₃); mass spectrum: 314(36), 139(100).

EXAMPLE 56

1.7 ml (12.3 mmol) of triethylamine are added dropwise to a mixture of 3.4 g (11 mmol) of $N^1$-($\alpha,\alpha,\alpha$-trifluoro-o-tolyl)-2,6-difluorobenzamidrazone and 0.9 ml (12.6 mmol) of acetyl chloride in 60 ml of toluene at 60° C. The mixture is then heated slowly to reflux temperature and held at this temperature for 18 hours. Subsequently, the reaction mixture is washed once with water and then extracted four times with 10 ml of concentrated hydrochloric acid each time. The combined, acidic aqueous extracts are neutralized with ice-cold sodium hydroxide solution and extracted twice with 50 ml of diethyl ether each time, and the combined organic phases are dried over anhydrous magnesium sulfate and evaporated under reduced pressure. The residue is purified by chromatography on silica gel ($\phi$ 40–63 μm) with n-hexane/ethyl acetate (3:2) and subsequently recrystallized from diisopropyl ether/n-hexane. In this manner there is obtained as a white crystallizate 3-(2,6-difluorophenyl)-5-methyl-1-($\alpha,\alpha,\alpha$-trifluoro-o-tolyl)-1H-1,2,4-triazole, m.p. 80°–82° C.; ¹H—NMR (CDCl₃, 60 MHz): 2.42 (s,CH₃); mass spectrum: 339(49), 298(56), 159(100).

The 3-(2,6-difluorophenyl)-5-methyl-1-($\alpha,\alpha,\alpha$-trifluoro-o-tolyl)-1H-1,2,4-triazole can also be manufactured as follows:

A solution of 72.5 g (0.23 mmol) of $N^1$-($\alpha,\alpha,\alpha$-trifluoro-o-tolyl)-2,6-difluorobenzamidrazone in 143 g (1.4 mmol) of acetic anhydride is heated at reflux temperature for 3 hours and the reaction mixture is subsequently evaporated under reduced pressure. The residue is taken up in about 300 ml of methylene chloride and the solution is washed in each case once with dilute sodium hydroxide solution and semi-saturated sodium chloride solution, dried over anhydrous magnesium sulfate and evaporated under reduced pressure. The crude product is finally recrystallized once from methylene chloride/n-hexane. In this manner there is obtained 3-(2,6-difluorophenyl)-5-methyl-1-($\alpha,\alpha,\alpha$-trifluoro-o-tolyl)-1H-1,2,4-triazole, m.p. 82°–82.5° C.

An ethereal solution of the above product is saturated with dry hydrogen chloride. The precipitated crystals are filtered off and washed well with diethyl ether. In this manner there is obtained 3-(2,6-difluorophenyl)-5-methyl-1-($\alpha,\alpha,\alpha$-trifluoro-o-tolyl)-1H-1,2,4-triazole hydrochloride, m.p. 160°–165° C.

EXAMPLE 57

A solution of 41.7 g (0.13 mol) of $N^1$-($\alpha,\alpha,\alpha$-trifluoro-o-tolyl)-2-chloro-6-fluorobenzamidrazone in 77 g (0.75 mol) of acetic anhydride is heated at reflux temperature for 90 minutes and thereafter added to sodium bicarbonate solution. The aqueous mixture is extracted twice with 100 ml of diethyl ether each time and the combined extracts are shaken out three times with concentrated hydrochloric acid. The combined aqueous phases are neutralized with sodium hydroxide solution and extracted with fresh diethyl ether, and the organic phase is washed with sodium chloride solution, dried over anhydrous magnesium sulfate and evaporated under reduced pressure. After recrystallization of the residue from diethyl ether/n-hexane there is obtained pure 3-(2-chloro-6-fluorophenyl)-5-methyl-1-($\alpha,\alpha,\alpha$-trifluoro-o-tolyl)-1H-1,2,4-triazole, m.p. 102°–103.5° C.; ¹H—NMR (CDCl₃, 60 MHz): 2.40 (s,CH₃); mass spectrum: 355(40), 314(52), 159(100).

EXAMPLES 58–67

The corresponding amidrazone of formula V is reacted with acetyl chloride or acetic anhydride analogously to the methods described in Example 56 and 57 in order to manufacture the compounds of formula I listed in Table 3 hereinafter.

TABLE 3

| Example | R¹ | R² | R³ | Physical data |
|---|---|---|---|---|
| 58 | o-Chlorophenyl | 2,6-Difluorophenyl | Methyl | M.p. 123–124.5° C. ¹H—NMR (CDCl₃, 60 MHz): 2.47 (s, CH₃) Mass spectrum: 305(29) 264(21), 125(100) |
| 59 | o-Tolyl | o-Chlorophenyl | " | B.p. 160° C./0.015 mmHg (2.00 Pa); ¹H—NMR (CDCl₃, 60 MHz): 2.19 (s, CH₃), 2.39 (s Mass spectrum: 282(82 268(28), 242(9), 105( |
| 60 | o-Bromophenyl | " | " | Oil ¹H—NMR (CDCl₃, 60 MHz): 2.42 (s, CH₃) Mass spectrum: 347/34 306/308(53), 169/171( |
| 61 | 2-Ethyl-6-methylphenyl | 2,6-Difluorophenyl | " | M.p. 96.5–97° C. ¹H—NMR (CDCl₃, 60 MHz): 2.05 (s, CH₃), 2.34 (s, CH₃), 2.37 (q, CH₂C Mass spectrum: 313(67 298(100) |
| 62 | 6-Chloro-o-tolyl | 2,6-Difluorophenyl | Methyl | M.p. 139° C. ¹H—NMR (CDCl₃, 60 MHz), 2.16 (s, CH₃), 2.40 (s, CH₃) Mass spectrum: 319(49), 304(40), 139(100) |
| 63 | 2-Chloro-5-trifluoromethylphenyl | " | " | M.p. 81–83° C. ¹H—NMR (CDCl₃, 60 MHz): 2.49 (s, CH₃) Mass spectrum: 373(18), 332(15), 193(100) |
| 64 | 4-Chloro-2-tri- | " | " | M.p. 81–82° C. |

TABLE 3-continued

| Example | R¹ | R² | R³ | Physical data |
|---|---|---|---|---|
|  | fluoromethyl-phenyl |  |  | ¹H—NMR (CDCl₃, 60 MHz): 2.40 (s, C$\underline{H}$₃) Mass spectrum: 373(27), 332(23), 193(100) |
| 65 | α,α,α-Trifluoro-o-tolyl | 2,6-Dichlorophenyl | " | M.p. 148–150° C. ¹H—NMR (CDCl₃, 60 MHz) 2.41 (s, C$\underline{H}$₃) |
| 66 | 2,4-Dichlorophenyl | 2-Chloro-6-fluorophenyl | " | M.p. 96° C. ¹H—NMR (CDCl₃, 400 MHz): 2.45 (s, C$\underline{H}$₃) Mass spectrum: 355(19), 314(19), 159(100) |
| 67 | o-Chlorophenyl | 2-Chloro-6-fluorophenyl | Methyl | M.p. 104° C. ¹H—NMR (CDCl₃, 400 MHz): 2.42 (s, C$\underline{H}$₃) Mass spectrum: 321(20), 280(17), 125(100) |

EXAMPLE 68

2.5 g (8 mmol) of N¹-(α,α,α-trifluoro-o-tolyl)-2,6-difluorobenzamidrazone are dissolved in 12.6 g (60 mmol) of trifluoroacetic anhydride, whereby the temperature of the solution rises to 35° C. The solution is heated at reflux temperature for 2 hours with continuous stirring and subsequently poured onto ice/water. The aqueous mixture is made alkaline with 28% sodium hydroxide solution and extracted twice with diethyl ether, and the combined organic phases are washed in sequence with dilute hydrochloric acid, sodium bicarbonate solution and sodium chloride solution, dried over anhydrous magnesium sulfate and evaporated under reduced pressure. After recrystallization of the residue from diethyl ether/n-hexane there is obtained 3-(2,6-difluorophenyl)-5-trifluoromethyl-1-(α,α,α-trifluoro-o-tolyl)-1H-1,2,4-triazole, m.p. 90° C.; mass spectrum: 393(100), 298(26), 159(82).

EXAMPLES 69–71

The corresponding amidrazone of formula V is reacted with trifluoroacetic anhydride analogously to the procedure described in Example 68 in order to manufacture the compounds of formula I listed in Table 4 hereinafter.

of triethylamine, and the mixture is heated at 100° C. for 24 hours. The mixture is heated at 162° C. for a further hour. Upon cooling the reaction product becomes solid for the most part, and the solvent is decanted off and the crystallizate is suspended in water. The product is filtered off and washed well with diethyl ether. In this manner there is obtained pure 1,3-bis-(o-chlorophenyl)-1,4-dihydro-1H-1,2,4-triazol-5-one, m.p. 231° C.; IR spectrum: 1695 cm⁻¹.

EXAMPLE 73

The 3-(o-chlorophenyl)-1-(α,α,α-trifluoro-o-tolyl)-1,4-dihydro-1H-1,2,4-triazol-5-one which is required as the starting material for the manufacture of the compound of Example 2 can be produced as follows:

A mixture of 5.0 g (20 mmol) of ethyl(o-chloro-α-ethoxybenzylidene)carbamate and 3.8 g (21 mmol) of o-trifluoromethylphenylhydrazine in 50 ml of carbon tetrachloride is heated to reflux temperature for about 16 hours. The mixture is subsequently diluted with 80 ml of methylene chloride, washed with 5% sodium bicarbonate solution, dried over anhydrous sodium sulfate and evaporated under reduced pressure. The crude product is dissolved in diethyl ether, and the solution is freed from insoluble constituents by filtration and treated with n-hexane. There thus precipitate white

TABLE 4

| Example | R¹ | R² | R³ | Physical data |
|---|---|---|---|---|
| 69 | o-Chlorophenyl | 2,6-Difluorophenyl | Trifluoromethyl | M.p. 98–98.5° C. Mass spectrum: 359(61), 364(7), 125(100) |
| 70 | 4-Chloro-2-trifluoromethylphenyl | " | " | B.p. 120° C./0.04 mmHg (5.33 Pa) Mass spectrum: 427(44), 332(8), 193(100) |
| 71 | α,α,α-Trifluoro-o-tolyl | 2,6-Dichlorophenyl | " | M.p. 100° C. Mass spectrum: 425(67), 330(20), 159(100) |

II. Preparation of the starting materials of formulae II, III, V and XII

EXAMPLE 72

The 1,3-bis-(o-chlorophenyl)-1,4-dihydro-1H-1,2,4-triazol-5-one which is required as the starting material for the manufacture of the compound of Example 1 can be produced as follows:

24.0 g (94 mmol) of ethyl (o-chloro-α-ethoxybenzylidene)carbamate and 16.8 g (94 mmol) of o-chlorophenylhydrazine hydrochloride are placed in 40 ml of 1,2-dichlorobenzene and treated with 13.1 ml (94 mmol)

crystals of ethyl [o-chloro-α-(o-trifluoromethylphenylhydrazino)-benzylidene]carbamate; m.p. 110°–113° C.; IR spectrum: 1740 cm⁻¹.

1.65 g (4.3 mmol) of the above intermediate are heated to 200° C. in a bulb tube under reduced pressure for 30 minutes, whereby the melt which results initially finally crystallizes. In this manner there is obtained 3-(o-chlorophenyl)-1-(α,α,α-trifluoro-o-tolyl)-1,4-dihydro-1H-1,2,4-triazol-5-one, m.p. 241°–244° C.; IR spectrum: 1695 cm⁻¹.

The end product of this Example can also be produced analogously to the process of Example 72, i.e. using o-trifluoromethylphenylhydrazine hydrochloride.

EXAMPLE 74

The 3-(2,6-difluorophenyl)-1-(α,α,α-trifluoro-o-tolyl)-1,4-dihydro-1H-1,2,4-triazol-5-one which is required as the starting material for the manufacture of the compound of Example 3 and 36 can be produced as follows:

A mixture of 16.0 g (62.2 mmol) of ethyl (2,6-difluoro-α-ethoxybenzylidene)carbamate and 11.0 g (62.2 mmol) of α,α,α-trifluoro-o-tolylhydrazine in 30 ml of 1,2-dichlorobenzene is heated to 135° C. for 18 hours while distilling off the ethanol which results. The separated solid is then filtered off and washed with diethyl ether. There is obtained pure 3-(2,6-difluorophenyl)-1-(α,α,α-trifluoro-o-tolyl)-1,4-dihydro-1H-1,2,4-triazol-5-one, m.p. 290° C.; IR spectrum (KBr): 1695 cm$^{-1}$; mass spectrum: 341(68), 298(26), 159(100).

EXAMPLE 75

The 3-(2,6-difluorophenyl)-1-(α,α,α-trifluoro-o-tolyl)-1,4-dihydro-1H-1,2,4-triazol-5-one can also be produced as follows:

2.0 g (6.3 mmol) of N$^1$-(α,α,α-trifluoro-o-tolyl)-2,6-difluorobenzamidrazone are placed in 8 ml of pyridine and treated while cooling well with 0.75 g (7.0 mmol) of ethyl chloroformate. The mixture is stirred for 1 hour and then heated to reflux temperature for 16 hours. The reaction mixture is poured onto ice/water, and the precipitated crystals are filtered off, washed well with diethyl ether and dried. In this manner there is obtained 3-(2,6-difluorophenyl)-1-(α,α,α-trifluoro-o-tolyl)-1,4-dihydro-1H-,1,2,4-triazol-5-one as crystals, m.p. 259°–260° C.; IR spectrum (KBr): 1695 cm$^{-1}$.

EXAMPLES 76–107

The corresponding starting materials of formulae XII and IV are reacted with one another analogously to the procedure described in Example 72, 73, 74 or 75 in order to produce the compounds of formula II listed in Table 5 hereinafter. The respective end products of formula I are also given in this Table.

TABLE 5

| Example | Example No. of the end product of formula I | R$^1$ | R$^2$ | Physical data |
| --- | --- | --- | --- | --- |
| 76 | 10 | o-Tolyl | o-Chlorophenyl | M.p. 194° C.; IR Spectrum 1690 cm$^{-1}$; mass spectrum: 285(95), 148(56), 104(100) |
| 77 | 6 | α,α,α-Trifluoro-o-tolyl | 2-Chloro-4-fluorophenyl | M.p. 203° C. mass spectrum: 357(43), 314(19), 159(100) |
| 78 | 4 | o-Chlorophenyl | " | M.p. 208° C. mass spectrum: 323(17), 288(31), 125(100) |
| 79 | 5 | " | 2,6-Difluorophenyl | M.p. 258° C. mass spectrum: 307(20), 272(31), 125(100) |
| 80 | 7 | α,α,α-Trifluoro-o-tolyl | 2-Chloro-6-fluorophenyl | M.p. 230° C. mass spectrum: 357(34), 314(20), 159(100) |
| 81 | 8 | o-Chlorophenyl | " | M.p. 223° C. IR spectrum (KBr): 1658 cm$^{-1}$; mass spectrum: 323(17), 288(30), 125(100) |
| 82 | 9 | 3,4-Dichlorophenyl | 2,6-Difluorophenyl | M.p. above 250° C. IR: 1725 cm$^{-1}$ Mass spectrum: 341(53), 298(7), 159(100) |
| 83 | 11 | α,α,α-Trifluoro-o-tolyl | o-Iodophenyl | M.p. 213° C. |
| 84 | 12 | 2-Chloro-6-methylphenyl | o-Chlorophenyl | M.p. 252° C. IR: 1695 cm$^{-1}$ Mass spectrum: 319(47), 284(100) |
| 85 | 13 | 4-Chloro-o-tolyl | " | M.p. 252–254° C. IR: 1695 cm$^{-1}$ |
| 86 | 14 | 3-Chloro-o-tolyl | " | M.p. above 250° C. IR: 1695 cm$^{-1}$ Mass spectrum: 319(75), 138(100) |
| 87 | 15 | 5-Chloro-o-tolyl | " | M.p. above 255° C. IR: 1695 cm$^{-1}$ Mass spectrum: 319(100) |
| 88 | 16 | 2-Chloro-5-trifluoromethylphenyl | o-Chlorophenyl | M.p. 198° C. IR: 1705 cm$^{-1}$ Mass spectrum: 373(54) 193(100) |
| 89 | 17 | 2-Chloro-6-fluorophenyl | " | - (not isolated) |
| 90 | 18 | o-Tolyl | 2,6-Difluoro- | M.p. 174–176° C. |

TABLE 5-continued

| Example | Example No. of the end product of formula I | R¹ | R² | Physical data |
|---|---|---|---|---|
| 91 | 19 | Phenyl | phenyl | IR: 1695/1710 cm$^{-1}$<br>M.p. 183° C.<br>IR: 1700 cm$^{-1}$ |
| 92 | 20 | 3,5-Dichlorophenyl | " | M.p. above 250° C.<br>IR: 1725 cm$^{-1}$<br>Mass spectrum: 341(93) 298(23), 159(100) |
| 93 | 21 | 2,4-Dimethylphenyl | " | M.p. 197.5–198.5° C.<br>IR: 1700 cm$^{-1}$<br>Mass spectrum: 301(10 |
| 94 | 22 | Phenyl | o-Chlorophenyl | M.p. 182° C. |
| 95 | 23 | α,α,α-Trifluoro-m-tolyl | 2,6-Dimethoxyphenyl | M.p. 187–188° C.<br>IR: 1710 cm$^{-1}$<br>$^1$H—NMR [(CH$_3$)$_2$SO, 60 MHz]: 3.85 (s, 2 × OC$\underline{H}_3$) |
| 96 | 24 | " | 2,6-Difluorophenyl | M.p. 219° C.<br>IR: 1720 cm$^{-1}$ |
| 97 | 25 | 3-Chloro-o-tolyl | " | M.p. 240° C.<br>IR: 1710 cm$^{-1}$<br>Mass spectrum: 321(100) |
| 98 | 26 | " | 2-Chloro-6-fluorophenyl | M.p. 155–160° C. |
| 99 | 27 | 2,3-Dimethylphenyl | o-Chlorophenyl | M.p. 201–203° C.<br>IR: 1695 cm$^{-1}$<br>Mass spectrum: 299(100) 282(53), 162(64) |
| 100 | 28 | " | 2,6-Difluorophenyl | M.p. 250–254° C.<br>IR: 1700 cm$^{-1}$<br>Mass spectrum: 301(100 |
| 101 | 29 | m-Fluorophenyl | o-Chlorophenyl | M.p. 224–226° C.<br>IR: 1708 cm$^{-1}$ |
| 102 | 30 | o-Nitrophenyl | o-Chlorophenyl | - (not isolated) |
| 103 | 31 | o-Bromophenyl | 2,6-Difluorophenyl | M.p. 280–281° C.<br>IR: 1702 cm$^{-1}$ |
| 104 | 32 | o-Methoxyphenyl | o-Chlorophenyl | IR: 1690 cm$^{-1}$ |
| 105 | 33 | o-Fluorophenyl | " | M.p. 185° C.<br>IR: 1705 cm$^{-1}$ |
| 106 | 34 | 3-Chloro-2-cyanophenyl | " | M.p. 285° C.<br>IR: 1755 cm$^{-1}$<br>Mass spectrum: 330(100), 295(63) |
| 107 | 35 | o-Cyanophenyl | " | - (not isolated) |

EXAMPLE 108

The ethyl N-acetyl-o-chlorobenzimidate which is required as the starting material for the manufacture of the compounds of Examples 38, 45, 46, 54 and 55 can be produced as follows:

A mixture of 41 g (22.3 mmol) of ethyl o-chlorobenzimidate and 25 g (25 mmol) of triethylamine in 500 ml of methylene chloride is treated dropwise with 19.5 g (24.8 mmol) of acetyl chloride, the temperature being held at 40° C. by the use of cooling. The reaction mixture is stirred at room temperature for a further 30 minutes, and the mixture is then washed in sequence with water, 5% sodium bicarbonate solution and semi-saturated sodium chloride solution, dried over anhydrous magnesium sulfate and evaporated under reduced pressure. After distillation of the crude product at 110° C./0.16 mmHg (21.33 Pa) there is obtained ethyl N-acetyl-o-chlorobenzimidate as a colourless liquid.

EXAMPLES 109–118

The corresponding alkyl benzimidate of formula XI is reacted with the corresponding carboxylic acid chloride analogously to the procedure described in Example 108 in order to produce the starting materials of formula III listed in Table 6 hereinafter. The respective end products of formula I are also given in this Table.

TABLE 6

| Example | Example No. of the end product of formula I | R² | R³' | R⁵ | Physical data |
|---|---|---|---|---|---|
| 109 | 39 | 2-Chloro-4-fluorophenyl | Methyl | Ethoxy | Oil<br>$^1$H—NMR (CDCl$_3$, 60 MHz): 2.07 (s, COCH$_3$), 4.37 (q, OC$\underline{H}_2$CH$_3$)<br>Mass spectrum: 208(72) 157(85), 43(100) |
| 110 | 40 | o-Fluorophenyl | " | " | Oil<br>$^1$H—NMR (CDCl$_3$, 60 |

TABLE 6-continued

| Example | Example No. of the end product of formula I | R² | R³' | R⁵ | Physical data |
|---|---|---|---|---|---|
| | | | | | MHz): 2.14 (d,$J_{F-H}$ = 1.5Hz, COC$\underline{H}_3$), 4.31 (q, OC$\underline{H}_2$CH₃) Mass spectrum: 166(26) 123(100) |
| 111 | 41 | 2,4-Dichloro-phenyl | " | " | Oil ¹H—NMR (CDCl₃, 60 MHz): 2.05 (s, COC$\underline{H}_3$), 4.34 (q, OC$\underline{H}_2$CH₃) Mass spectrum: 116(64) 173(66), 43(100) |
| 112 | 42 | o-Bromophenyl | " | " | Oil ¹H—NMR (CDCl₃, 60 MHz): 2.04 (s, COC$\underline{H}_3$), 4.34 (q, OC$\underline{H}_2$CH₃) |
| 113 | 43 | o-Tolyl | Methyl | Ethoxy | Oil ¹H—NMR (CDCl₃, 60 MHz): 1.98 (s, COC$\underline{H}_3$), 2.39 (s, C$\underline{H}_3$), 4.31 (q, OC$\underline{H}_2$CH₃) |
| 114 | 44 | o-Methoxy-phenyl | " | " | Oil ¹H—NMR (CDCl₃, 60 MHz): 2.13 (s, COC$\underline{H}_3$), 3.82 (s, OC$\underline{H}_3$), 4.32 (q, OC$\underline{H}_2$CH₃) Mass spectrum: 190(83), 135(100) |
| 115 | 49 | o-Chlorophenyl | Chloro-methyl | " | Oil |
| 116 | 47,50,52,53 | 2,6-Difluoro-phenyl | Methyl | " | B.p. 145° C./20 mmHg (2667 Pa); ¹H—NMR (CDCl₃, 60 MHz): 2.19 (s, COC$\underline{H}_3$), 4.38 (q, OC$\underline{H}_2$CH₃) Mass spectrum: 184(46), 141(100) |
| 117 | 48 | α,α,α-Trifluoro-o-tolyl | Methyl | Ethoxy | B.p. 75° C./0.1 mmHg (13.33 Pa); ¹H—NMR (CDCl₃ 60 MHz): 1.96 (s, COC$\underline{H}_3$), 4.32 (q, OC$\underline{H}_2$CH₃) |
| 118 | 51 | o-Iodophenyl | " | " | Oil ¹H—NMR (CDCl₃, 60 MHz): 2.05 (s, COC$\underline{H}_3$), 4.37 (q, OC$\underline{H}_2$CH₃) |

EXAMPLE 119

The N¹-(o-tolyl)-o-chlorobenzamidrazone which is required as the starting material for the manufacture of the compound of Example 59 can be produced as follows:

A mixture of 2.4 g (13 mmol) of ethyl o-chlorobenzimidate, 2,1 g (13 mmol) of o-tolylhydrazine hydrochloride and 1.8 ml (13 mmol) of triethylamine is stirred for about 16 hours in 25 ml of ethylene chloride. The reaction mixture is then washed with water and the organic phase is dried over anhydrous magnesium sulfate and evaporated under reduced pressure. There is thus obtained crude N¹-(o-tolyl)-o-chlorobenzamidrazone (m.p. 148°–150° C. after crystallization from methylene chloride/n-hexane).

EXAMPLE 120

The N¹-(α,α,α-trifluoro-o-tolyl)-2,6-difluorobenzamidrazone which is required as the starting material for the manufacture of the compounds of Examples 56 and 68 can be produced as follows:

106 g (0.5 mol) of o-trifluoromethylphenylhydrazine hydrochloride are introduced portionwise at 0° C. into a solution of 93 g (0.5 mol) of ethyl 2,6-difluorobenzimidate in 250 ml of pyridine and the reaction mixture is stirred at 0° C. for 4 hours and subsequently at room temperature for a further 16 hours. The mixture is diluted with about 750 ml of diethyl ether and washed in each case once with water and saturated sodium chloride solution, and the organic phase is dried over anhydrous magnesium sulfate and evaporated under reduced pressure. After recrystallization of the crude product from diethyl ether/n-hexane there is obtained N¹-(α,α,α-trifluoro-o-tolyl)-2,6-difluorobenzamidrazone, m.p. 107°–108° C.

EXAMPLES 121–127

The corresponding ethyl benzimidate of formula XI' is reacted with the corresponding phenylhydrazine hydrochloride of formula IV analogously to the methods described in Examples 119 and 120 in order to produce the starting materials (amidrazones) of formula V listed in Table 7 hereinafter. The respective end products of formula I are also given in this Table.

TABLE 7

| Example | Example No. of the end product of formula I | R¹ | R² | Physical data |
|---|---|---|---|---|
| 121 | 58,69 | o-Chlorophenyl | 2,6-Difluorophenyl | M.p. 107–108° C. |
| 122 | 60 | o-Bromophenyl | o-Chlorophenyl | M.p. 123–126° C. |
| 123 | 61 | 2-Ethyl-6-methylphenyl | 2,6-Difluorophenyl | — |
| 124 | 62 | 6-Chloro-o-tolyl | " | $^1$H—NMR (CDCl$_3$, 60 MHz): 2.35 (s, CH$_3$), 5.10 (broad signal, NH$_2$), 6.15 (broad signal, NH) |
| 125 | 63 | 2-Chloro-5-trifluoromethylphenyl | " | $^1$H—NMR (CDCl$_3$, 60 MHz): 4.99 (broad signal, NH$_2$), 6.58 (broad signal, NH) |
| 126 | 64,70 | 4-Chloro-2-trifluoromethylphenyl | " | Mass spectrum: 349(34), 332(16), 193(100) |
| 127 | | o-Chlorophenyl | o-Chlorophenyl | M.p. 139–140.5° C. |

EXAMPLE 128

The N$^1$-($\alpha,\alpha,\alpha$-trifluoro-o-tolyl)-2-chloro-6-fluorobenzamidrazone which is required as the starting material for the manufacture of the compound of Example 57 can be produced as follows:

71.7 g (0.37 mol) of 2-chloro-6-fluorobenzoyl chloride are slowly added dropwise to a solution, cooled to 5° C., of 65.4 g (0.37 mol) of o-trifluoromethylphenylhydrazine in 200 ml of pyridine in such a manner that the temperature of the reaction mixture does not exceed 5° C. The mixture is stirred at room temperature for a further 90 minutes and subsequently treated with 400 ml of water. The aqueous phase is extracted three times with 150 ml of diethyl ether each time and the combined organic phases are washed in sequence with 2N sodium hydroxide solution and concentrated sodium chloride solution. The organic phase is then dried over anhydrous sodium sulfate and evaporated under reduced pressure, the crude product being evaporated twice with a small amount of toluene in order to remove excess pyridine. After recrystallization from methylene chloride/n-hexane there is obtained N$^1$-($\alpha,\alpha,\alpha$-trifluoro-o-tolyl)-2-chloro-6-fluorobenzhydrazide, m.p. 147°–148° C.; mass spectrum: 332(19), 157(100).

A suspension of 117.4 g (0.35 mol) of the above product in 61.4 g (0.40 mol) of phosphorus oxychloride is heated at reflux temperature for 90 minutes. Thereafter, the cooled reaction mixture is poured into ice-cold sodium bicarbonate solution and the whole is extracted twice with 200 ml of diethyl ether each time. The combined organic phases are washed with sodium chloride solution, dried over anhydrous magnesium sulfate and evaporated under reduced pressure. After taking up the residue in n-hexane the insoluble constituents are filtered off and the filtrate is evaporated to dryness under reduced pressure. In this manner there is obtained N$^1$-($\alpha,\alpha,\alpha$-trifluoro-o-tolyl)-2-chloro-6-fluorobenzhydrazinoyl chloride, mass spectrum: 350(37), 314(39), 159(100).

89.7 g (0.28 mol) of the above product are taken up in 90 ml of diethyl ether and the solution is treated at −50° C. to −40° C. with 90 ml of 25% aqueous ammonia solution during 10 minutes while stirring vigorously. The reaction mixture is left to come to 0° C. during 90 minutes and the aqueous phase is separated. The organic phase is then extracted three times with dilute hydrochloric acid, and the combined, aqueous acidic extracts are neutralized with sodium hydroxide solution and subsequently extracted with fresh diethyl ether. The organic phase is dried over anhydrous magnesium sulfate and evaporated under reduced pressure. After recrystallization of the residue from n-hexane there is obtained pure N$^1$-($\alpha,\alpha,\alpha$-trifluoro-o-tolyl)-2-chloro-6-fluorobenzamidrazone, m.p. 132.5° C.

EXAMPLES 129–131

Analogously to the methods described in Example 128, the corresponding benzoyl chloride of formula XV is reacted with the corresponding phenylhydrazine of formula IV, the thus-obtained N-phenyl-benzhydrazide of formula XVI is treated with a chlorinating agent and finally the N-phenyl-benzhydrazinoyl chloride of formula XIV obtained in this manner is subjected to an aminolysis in order to produce the starting materials (amidrazones) of formula V listed in Table 8 hereinafter. The respective end products of formula I are also given in this Table.

TABLE 8

| Example | Example No. of the end product of formula I | R¹ | R² | Physical data |
|---|---|---|---|---|
| 129 | 65,71 | $\alpha,\alpha,\alpha$-Trifluoro-o-tolyl | 2,6-Dichlorophenyl | $^1$H—NMR (CDCl$_3$, 60 MHz): 4.90 (broad signal, NH$_2$), 6.45 (broad signal, NH) Mass spectrum: 347(33), 330(31), 159(100) |
| 130 | 66 | 2,4-Dichlorophenyl | 2-Chloro-6-fluorophenyl | - (not isolated) |

TABLE 8-continued

| Example | Example No. of the end product of formula I | R¹ | R² | Physical data |
|---|---|---|---|---|
| 131 | 67 | o-Chlorophenyl | " | M.p. 162-163° C. |

The compounds of Examples 119-127 can also be produced in an analogous manner.

EXAMPLE 132

The ethyl (o-chloro-α-ethoxybenzylidene)carbamate which is required as the starting material for the production of the 1,4-dihydro-1H-1,2,4-triazol-5-ones of Examples 72, 73, 76, 84-89, 94, 99, 101, 102 and 104-107 can be produced as follows:

A mixture of 40 g (22 mmol) of ethyl o-chlorobenzimidate and 22.2 g (21 mmol) of 2,6-lutidine in 500 ml of petroleum ether (b.p. 100°-130° C.) is treated with 27.2 g (25 mmol) of ethyl chloroformate and the whole is then heated at reflux temperature for about 16 hours. The precipitated salt is subsequently filtered off, the filtrate is evaporated under reduced pressure and the residue is recrystallized from diethyl ether. In this manner there is obtained ethyl (o-chloro-α-ethoxybenzylidene)carbamate, m.p. 65°-66° C.; $^1$H—NMR (CDCl$_3$, 60 MHz): 4.02 (q,OC$\underline{H}_2$CH$_3$), 4.58 (q, OCH$_2$C$\underline{H}_3$); mass spectrum: 220(100).

EXAMPLES 133-137

The corresponding ethyl benzimidate of formula XI is reacted with ethyl chloroformate analogously to the procedure described in Example 132 in order to produce the starting materials of formula XII listed in Table 9 hereinafter. The respective end products of formula II are also given in this Table.

TABLE 9

| Example | Example No. of the end product of formula II | R² | R⁴ | R⁶ | Physical data |
|---|---|---|---|---|---|
| 133 | 74,79,82 90-93,96 97,100,103 | 2,6-Difluoro-phenyl | Ethoxy | Ethoxy | B.p. 115° C./0.8 mmHg (106.67 Pa) $^1$H—NMR (CDCl$_3$, 60 MHz): 4.14 (q, OC$\underline{H}_2$CH$_3$), 4.44 (q, OC$\underline{H}_2$CH$_3$) |
| 134 | 77,78 | 2-Chloro-4-fluorophenyl | " | " | Oil |
| 135 | 80,81,98 | 2-Chloro-6-fluorophenyl | " | " | B.p. 100° C./0.02 mmHg (2.67 Pa) $^1$H—NMR (CDCl$_3$, 60 MHz): 4.07 (q, OC$\underline{H}_2$CH$_3$), 4.45 (q, OC$\underline{H}_2$CH$_3$) |
| 136 | 83 | o-Iodophenyl | " | " | Oil $^1$H—NMR (CDCl$_3$, 60 MHz): 3.99 (q, OC$\underline{H}_2$CH$_3$), 4.39 (q, OC$\underline{H}_2$CH$_3$) |
| 137 | 95 | 2,6-Dimethoxy-phenyl | " | " | M.p. 73-74° C. $^1$H—NMR (CDCl$_3$, 60 MHz): 3.81 (s, OC$\underline{H}_3$), 4.01 (q, OC$\underline{H}_2$CH$_3$), 4.40 (q, OC$\underline{H}_2$CH$_3$) |

III. Formulation Examples

EXAMPLE 138

An emulsifiable concentrate has the following composition:

| | g/liter |
|---|---|
| Compound of formula I (active substance) | 250 |
| Polyarylphenol-(18) ethoxylate | 300 |
| Polyvinylpyrrolidone emulsifiers | 20 |
| Isotridecyl alcohol | 20 |
| N—Methyl-2-pyrrolidone (solvent) ad | 1 liter |

The active substance and the emulsifiers are dissolved in the solvent. After dilution with water the thus-obtained emulsifiable concentrate gives an emulsion which is well suited as a spray liquor.

EXAMPLE 139

An emulsifiable concentrate has the following composition:

| | g/liter |
|---|---|
| Compound of formula I (active substance) | 250 |
| Nonylphenyl-(10) ethoxylate (emulsifiers) | 75 |
| Calcium dodecylbenzene sulfonate | 25 |
| N—Methyl-2-pyrrolidone | 400 |
| Mixture of mono-, di- and (solvents) tri(lower alkyl)benzenes ad | 1000 ml |

The active substance and the two emulsifiers are dissolved in the first solvent and the volume is subsequently made up to 1 l by adding the second solvent. After dilution with water the thus-obtained emulsifiable concentrate gives an emulsion which is well suited as a spray liquor.

EXAMPLE 140

A spray powder has the following composition:

| | Weight percent |
|---|---|
| Compound of formula I (active substance) | 50 |
| Sodium lauryl sulfate (wetting/dispersing agent) | 1 |
| Sodium lignosulfonate (dispersing agent) | 2 |
| Hydrated silicic acid (about 87% SiO$_2$) (inert, pulverous) | 5 |
| Kaolin (mainly carrier substances) Al$_2$(Si$_2$O$_5$)(OH)$_4$) | 42 |
| | 100 |

The active substance is mixed homogeneously with the remaining formulation components in a suitable apparatus. The resulting powder is then finely ground in a suitable milling aggregate (e.g. pin, hammer, ball or air-jet mill) to a particle size which is required for an optimum biological activity and thereafter again mixed. The thus-obtained spray powder is spontaneously wetted with water and gives well-suspended, ready-for-use spray liquors.

What is claimed is:

1. A compound of the formula

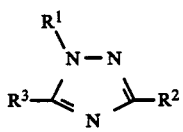

I wherein

R$^1$ is phenyl or phenyl substituted with 1 to 3 chlorine atoms, a bromine atom, an iodine atom, 1 to 3 fluorine atoms, 1 or 2 C$_{1-2}$-alkyl groups, 1 or 2 halomethyl groups, a C$_{1-2}$-alkoxy group, a C$_{1-2}$-haloalkoxy group, a nitro group and/or a cyano group, R$^2$ is phenyl substituted with 1 or 2 chlorine atoms, a bromine atom, an iodine atom, 1 to 3 fluorine atoms, 1 or 2 C$_{1-2}$-alkyl groups, a halomethyl group and/or 1 or 2 methoxy groups, at least one of the substituents being situated in an o-position, and R$^3$ is halogen or methyl, as well as the acid addition salts of the compounds of formula I.

2. The compound according to claim 1 wherein R$^3$ is halogen.

3. The compound according to claim 2 wherein R$^2$ is mono- or disubstituted phenyl with the substituents being 1 or 2 fluorine atoms, 1 or 2 chlorine atoms, a bromine atom and/or an iodine atom.

4. The compound according to claim 3 wherein R$^2$ is o-chlorophenyl.

5. The compound according to claim 4 which is 5-chloro-3-(o-chlorophenyl)-1-(2,3-dimethylphenyl)-1H-1,2,4-triazole.

6. The compound according to claim 3 wherein R$^2$ is phenyl disubstituted with chlorine and/or fluorine.

7. The compound according to claim 6 which is 5-chloro-3-(2,6-difluorophenyl)-1-(2,3-dimethylphenyl)-1H-1,2,4-triazole.

8. The compound according to claim 4 or 6 wherein R$^1$ is phenyl mono-substituted with chlorine, fluorine or bromine.

9. The compound according to claim 8 which is 1,3-Bis(o-chlorophenyl)-5-chloro-1H-1,2,4-triazole.

10. The compound according to claim 8 which is 5-chloro-3-(o-chlorophenyl)-1-(o-fluorophenyl)-1H-1,2,4-triazole.

11. The compound according to claim 8 which is 5-chloro-1-(o-chlorophenyl)-3-(2-chloro-4-fluorophenyl)-1H-1,2,4-triazole.

12. The compound according to claim 8 which is 5-chloro-1-(o-chlorophenyl)-3-(2,6-difluorophenyl)-1H-1,2,4-triazole.

13. The compound according to claim 18 which is 5-chloro-1-(o-chlorophenyl)-3-(2-chloro-6-fluorophenyl)-1H-1,2,4-triazole.

14. The compound according to claim 8 which is 1-(o-bromophenyl)-5-chloro-3-(2,6-difluorophenyl)-1H-1,2,4-triazole.

15. The compound according to claim 4 or 6 wherein R$^1$ is phenyl or phenyl mono-substituted with a C$_{1-2}$-alkyl group.

16. The compound according to claim 15 which is 5-Chloro-3-(o-chlorophenyl)-1-(o-tolyl)-1H-1,2,4-triazole.

17. The compound according to claim 15 which is 5-chloro-3-(2,6-difluorophenyl)-1-(o-tolyl)-1H-1,2,4-triazole.

18. The compound according to claim 15 which is 5-chloro-3-(2,6-difluorophenyl)-1-phenyl-1H-1,2,4-triazole.

19. The compound according to claim 4 or 6 wherein R$^1$ is disubstituted phenyl wherein one substituent is a chlorine or fluorine atom and the other is a C$_{1-2}$-alkyl group.

20. The compound according to claim 19 which is 5-chloro-3-(o-chlorophenyl)-1-(3-chloro-o-tolyl)-1H-1,2,4-triazole.

21. The compound according to claim 19 which is 5-chloro-3-(o-chlorophenyl)-1-(5-chloro-o-tolyl)-1H-1,2,4-triazole.

22. The compound according to claim 19 which is 5-chloro-3-(2,6-difluorophenyl)-1-(3-chloro-o-tolyl)-1H-1,2,4-triazole.

23. The compound according to claim 19 which is 5-chloro-3-(2-chloro-6-fluorophenyl)-1-(3-chloro-o-tolyl)-1H-1,2,4-triazole.

24. The compound according to claim 4 or 6 wherein R$^1$ is phenyl mono-substituted with a trifluoromethyl group.

25. The compound according to claim 24 which is 5-chloro-3-(o-chlorophenyl)-1-($\alpha,\alpha,\alpha$-trifluoro-o-tolyl)-1H-1,2,4-triazole.

26. The compound according to claim 24 which is 5-chloro-3-(2-chloro-4-fluorophenyl)-1-($\alpha,\alpha,\alpha$-trifluoro-o-tolyl)-1H-1,2,4-triazole.

27. The compound according to claim 24 which is 5-chloro-3-(2-chloro-6-fluorophenyl)-1-($\alpha,\alpha,\alpha$-trifluoro-o-tolyl)-1H-1,2,4-triazole.

28. The compound according to claim 24 which is 5-chloro-3-(2,6-difluorophenyl)-1-($\alpha,\alpha,\alpha$-trifluoro-o-tolyl)-1H-1,2,4-triazole.

29. The compound according to claim 24 which is 3-(2-chloro-6-fluorophenyl)-5-fluoro-1-($\alpha,\alpha,\alpha$-trifluoro-o-tolyl)-1H-1,2,4-triazole.

30. The compound according to claim 24 which is 5-bromo-3-(2,6-difluorophenyl)-1-($\alpha,\alpha,\alpha$-trifluoro-o-tolyl)-1H-1,2,4-triazole.

31. The compound according to claim 1 wherein R$^3$ is methyl.

32. The compound according to claim 31 wherein R$^2$ is mono- or disubstituted phenyl with the substituents being 1 or 2 fluorine atoms, 1 or 2 chlorine atoms, a bromine atom and/or an iodine atom.

33. The compound according to claim 32 wherein $R^2$ is o-chlorophenyl.

34. The compound according to claim 32 wherein $R^2$ is phenyl disubstituted with chlorine and/or fluorine.

35. The compound according to claim 33 or 34 wherein $R^1$ is phenyl mono-substituted with chlorine, fluorine, a $C_{1-2}$-alkyl group or a trifluoromethyl group.

36. The compound according to claim 35 wherein $R^1$ is phenyl mono-substituted with a trifluoromethyl group.

37. The compound according to claim 36 which is 3-(o-chlorophenyl)-5-methyl-1-($\alpha,\alpha,\alpha$-trifluoro-o-tolyl)-1H-1,2,4-triazole.

38. The compound according to claim 36 which is 3-(2-chloro-4-fluorophenyl)-5-methyl-1-($\alpha,\alpha,\alpha$-trifluoro-o-tolyl)-1H-1,2,4-triazole.

39. The compound according to claim 36 which is 3-(2,6-difluorophenyl)-5-methyl-1-($\alpha,\alpha,\alpha$-trifluoro-o-tolyl)-1H-1,2,4-triazole.

40. The compound according to claim 36 which is 3-(2-chloro-6-fluorophenyl)-5-methyl-1-($\alpha,\alpha,\alpha$-trifluoro-o-tolyl)-1H-1,2,4-triazole.

41. A composition for the control of insects and mites which contains an effective amount of at least one compound of the formula

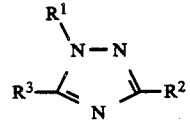

wherein
  $R^1$ is phenyl or phenyl substituted with 1 to 3 chlorine atoms, a bromine atom, an iodine atom, 1 to 3 fluorine atoms, 1 or 2 $C_{1-2}$-alkyl groups, 1 or 2 halomethyl groups, a $C_{1-2}$-alkoxy group, a $C_{1-2}$-haloalkoxy group, a nitro group and/or a cyano group,
  $R^2$ is phenyl substituted with 1 or 2 chlorine atoms, a bromine atom, an iodine atom, 1 or 2 fluorine atoms, 1 or 2 $C_{1-2}$-alkyl groups, a halomethyl group and/or 1 or 2 methoxy groups, at least one of the substitutents being situated in an o-position, and
  $R^3$ is halogen or methyl,
or an acid addition salt thereof, as well as formulation adjuvants.

42. A method for the control of pests, which method comprises treating the locus to be protected or the pests themselves with an effective amount of a compound in accordance with claim 1.

* * * * *